US006023977A

United States Patent [19]
Langdon et al.

[11] Patent Number: 6,023,977
[45] Date of Patent: Feb. 15, 2000

[54] ULTRASONIC IMAGING ABERRATION CORRECTION SYSTEM AND METHOD

[75] Inventors: Donald R. Langdon; Gregory L. Holley, both of Mountain View; John A. Hossack, Palo Alto, all of Calif.; Pai-Chi Li, Taipei, Taiwan

[73] Assignee: Acuson Corporation, Mountain View, Calif.

[21] Appl. No.: 09/061,082

[22] Filed: Apr. 15, 1998

Related U.S. Application Data

[63] Continuation-in-part of application No. 08/904,859, Aug. 1, 1997, abandoned.

[51] Int. Cl.[7] .............................. G01N 29/00; G01S 15/00
[52] U.S. Cl. ................................ 73/629; 600/443; 367/87
[58] Field of Search .............................. 73/611, 610, 609, 73/606, 602, 596, 627, 631, 614, 615, 616, 628, 629; 600/443, 447, 458; 367/87, 95

[56] References Cited

U.S. PATENT DOCUMENTS

| | | |
|---|---|---|
| 3,640,271 | 2/1972 | Horton . |
| 4,712,037 | 12/1987 | Verbeek et al. . |
| 5,040,537 | 8/1991 | Katakura . |
| 5,111,823 | 5/1992 | Cohen . |
| 5,115,809 | 5/1992 | Saitoh et al. . |
| 5,135,000 | 8/1992 | Akselrod et al. . |
| 5,190,766 | 3/1993 | Ishihara . |
| 5,195,520 | 3/1993 | Schlief et al. . |
| 5,197,477 | 3/1993 | Peterson et al. . |
| 5,215,680 | 6/1993 | D'Arrigo . |
| 5,219,401 | 6/1993 | Cathignol et al. . |
| 5,233,994 | 8/1993 | Shmulewitz . |
| 5,255,683 | 10/1993 | Monaghan . |
| 5,287,753 | 2/1994 | Routh et al. . |
| 5,313,948 | 5/1994 | Murashita et al. . |
| 5,348,013 | 9/1994 | Kanda et al. . |
| 5,357,962 | 10/1994 | Green ..................................... 600/443 |
| 5,358,466 | 10/1994 | Aida et al. . |
| 5,380,411 | 1/1995 | Schlief . |
| 5,386,830 | 2/1995 | Powers et al. . |

(List continued on next page.)

FOREIGN PATENT DOCUMENTS

| | | |
|---|---|---|
| 0 357 164 | of 0000 | European Pat. Off. . |
| 0 770 352 A1 | 5/1997 | European Pat. Off. . |
| WO 98/20361 | 5/1998 | WIPO . |

OTHER PUBLICATIONS

S. W. Flax and M. O'Donnell, "Phase–Aberration Correction Using Signals From Point Reflectors and Diffuse Scatterers: Basic Principles", *IEEE Transactions on Ultrasonics, Ferroelectrics, and Frequency Control*, vol. 35, No. 6, pp. 758–767, Nov. 1988.

Levin Nock and Gregg E. Trahey, "Phase aberration correction in medical ultrasound using speckle brightness as a quality factor", *J. Acoust. Soc. Am.*, vol. 85, No. 5, pp. 1819–1833, May 1989.

Daniel Rachlin, "Direct estimation of aberrating delays in pulse–echo imaging systems", *J. Acoust. Soc. Am.*, vol. 88, No. 1, pp. 191–198, Jul. 1990.

Mathias Fink, "Time Reversal of Ultrasonic Fields–Part I: Basic Principles", *IEEE Transactions on Ultrasonics, Ferroelectrics, and Frequency Control*, vol. 39, No. 5, pp. 555–566, Sep. 1992.

(List continued on next page.)

*Primary Examiner*—Richard A. Moller
*Attorney, Agent, or Firm*—Brinks Hofer Gilson & Lione

[57] ABSTRACT

An ultrasonic imaging system including an aberration correction system uses a harmonic component of the fundamental transmitted frequency for imaging, or for aberration correction, or both. By properly selecting the frequency pass bands of filters used in the image signal path and in the aberration correction signal path operating advantages are provided. The aberration correction values may be calculated concurrently with image formation.

52 Claims, 11 Drawing Sheets

U.S. PATENT DOCUMENTS

| | | |
|---|---|---|
| 5,396,285 | 3/1995 | Hedberg et al. . |
| 5,409,688 | 4/1995 | Quay . |
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |
| 5,433,207 | 7/1995 | Pretlow, III . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,469,849 | 11/1995 | Sasaki et al. . |
| 5,471,990 | 12/1995 | Thirsk . |
| 5,479,926 | 1/1996 | Ustuner et al. . |
| 5,482,046 | 1/1996 | Deitrich . |
| 5,523,058 | 6/1996 | Umemura et al. . |
| 5,526,816 | 6/1996 | Arditi . |
| 5,540,909 | 7/1996 | Schutt . |
| 5,558,092 | 9/1996 | Unger et al. . |
| 5,560,364 | 10/1996 | Porter . |
| 5,570,691 | 11/1996 | Wright et al. ........................... 600/447 |
| 5,577,505 | 11/1996 | Brock-Fisher et al. . |
| 5,579,768 | 12/1996 | Klesenski . |
| 5,579,770 | 12/1996 | Finger . |
| 5,580,575 | 12/1996 | Unger et al. . |
| 5,588,435 | 12/1996 | Weng et al. . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,628,322 | 5/1997 | Mine . |
| 5,632,277 | 5/1997 | Chapman et al. . |
| 5,678,554 | 10/1997 | Hossack et al. . |
| 5,696,737 | 12/1997 | Hossack et al. . |
| 5,724,976 | 3/1998 | Mine et al. . |

OTHER PUBLICATIONS

Dong–Lai Liu and Robert C. Waag, "Correction of ultrasonic wavefront distortion using backpropagation and a reference waveform method for time–shift compensation", *J. Acoust. Soc. Am.,* vol. 96, No. 2, pp. 649–660, Aug. 1994.

Sriram Krishnan, Pai–Chi Li and Matthew O'Donnell, "Adaptive Compensation of Phase and Magnitude Aberrations", *IEEE Transactions on Ultrasonics, Ferroelectrics, and Frequency Control,* vol. 43, No. 1, pp. 44–55, Jan. 1996.

Gary C Ng, Paul D. Freiburger, William F. Walker and Gregg E. Trahey, "A Speckle Target Adaptive Imaging Technique in the Presence on Distributed Aberrations", *IEEE Transactions on Ultrasonics, Ferroelectrics, and Frequency Control,* vol. 44, No. 1, pp. 140–151, Jan. 1997.

Ted Christopher, "Finite Amplitude Distortion–Based Inhomogeneous Pulse Echo Ultrasonic Imaging", *IEEE Transactions on Ultrasonics, Ferroelectrics, and Frequency Control,* vol. 44, No. 1, pp. 125–139, Jan. 1997.

Qing Zhu and Bernard Steinberg, "Deaberration of Incoherent Wavefront Distortion: An Approach Toward Inverse Filtering", *IEEE Transactions on Ultrasonics, Ferroelectrics, and Frequency Control,* vol. 44, No. 3, pp. 575–589, May 1997.

T.G. Leighton, "Transient excitation of insonated bubbles." Research Notes.

Eric J. Chen, et al., "Young's Modulus Measurements of Soft Tissues with Application to Elasticity Imaging." IEEE Transactions on Ultrasonics, Ferroelectrics, and Frequency Control, vol. 43, No. 1, Jan. 1996.

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1996.

Marc Gensane, "Bubble population measurements with a parametric array." 1994 Acoustical Society of America, 95 (6) Jun.

Ken Ishihara et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

Shmuel Gottlieb, M.D. et al., "Effect of Pressure on Echocardiographic Videodensity from Sonicated Albumin: An In Vitro Model." J. Ultrasound Med. 14 (1995).

J. W. Norris, "The non–linear oscillation of a radially symmetric bubble in a time periodic pressure field." Dynamics and Stability of Systems, vol. 9, No. 1 (1994).

Michael S. Longuet–Higgins, Resonance in nonlinear bubble oscillations. J. Fluid Mech. (1991) vol. 224.

Chiang C. Mei, et al., "Parametric resonance of a spherical bubble." J. Fluid Med. (1991) vol. 229.

V.L. Newhouse, et al., "Bubble size measurements using the nonlinear mixing of two frequencies." J. Acoust. Soc. Am. 75 (5), May 1984.

Janet B. Jones–Oliveira, et al., "Transient fluid–solid interaction of submerged spherical shells revisited: Proliferation of frequencies and acoustic radiation effects." Acoustical Society of America, 96(2), Pt. 1, Aug. 1994.

Chandra M. Sehgal, PhD., et al., "Sonographic Enhancement of Renal Cortex by Contrast Media." J. Ultrasound Med, 14 (1995).

"Abstract Session IV Contrast and Ischemia." and "Poster Session A New Technologies". Journal of the American Society of Echocardiography, vol. 8, No. 3, May 1995.

Chandra M. Sehgal, PhD., et al., "Influence of Postprocessing Curves on Contrast–Echocardiographic Imaging: Preliminary Studies." J. Ultrasound Med, 14 (1995).

Deborah J. Rubens, M.D., et al., "Sonoelasticity Imaging of Prostate Cancer: In Vitro Results." Radiology, vol. 995, No. 2, 1995.

Kotaro Sato, et al., "Numerical analysis of a gas bubble near a rigid boundary in an oscillatory pressure field." J. Acoustical Society of America, 95 (5), May 1994.

L.W. Anson et al., "Ultrasonic scattering from spherical shells including viscous and thermal effects." J. Acoustical Society of America, 93 (4), Apr. 1993.

B. Schrope, et al., "Simulated Capillary Blood Flow Measurement Using a Nonlinear Utrasonic Contrast Agent." Ultrasonic Imaging 14 (1992).

Fred Lee, Jr., M.D., et al., "Sonoelasticity Imaging: Results in in Vitro Tissue Specimens." Radiology, vol. 181, No. 1, 1991.

Kevin J. Parker, PhD, et al., "Sonoelasticity of Organs: Shear Waves Ring a Bell." J. Ultrasound Med., 11 (1992).

William Armstrong, M.D., et al., "American Society of Echocardiography Position Paper on Contrast Echocardiography." draft 1 –Jun. 6, 1994.

K.J. Parker, et al., "Tissue Response to Mechanical Vibrations for 'Sonoelasticity Imaging'." Ultrasound in Med. & Biol., vol. 16, No. 3, (1990).

Robert M. Lerner, et al., "'Sonoelasticity' Images Derived from Ultrasound Signals in Mechanically Vibrated Tissues." Ultrasound in Med. & Biol., vol. 16, No. 3, (1990).

J. Ophir, et al., "Elastography: A Quantitative Method for Imaging the Elasticity of Biological Tissues." Ultrasonics Imaging 13 (1991).

J.A. Hossack et al., "Improving transducer performance using multiple active layers." SPIE vol. 1733 (1992).

Volkmar Uhlendorf, et al., "Nonlinear Acoustical Response of Coated Microbubbles in Diagnostic Ultrasound." 1994 Ultrasonics Symposium.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

H. Edward Karrer, et al,. "A Phased Array Acoustic Imaging System for Medical Use." 1980 Ultrasonics Symposium.

"HP Ultrasound Technolgies—Viability." About HP Ultrasound Imaging, WWW document, 1997.

"Supplement to Journal of the American College of Cardiology" American College of Cardiology, 45th Annual Scientific Session, Mar. 24–27, 1996, pp. 21A, 63A, 239–240A.

Yang–Sub Lee, et al., "Time–domain modeling of pulsed finite–amplitude sound beams." 1995 Acoustical Society of America, 97 (2), Feb. 1995.

Michalakis A. Averkiou, et al., "Self–demodulation of amplitude–and–frequency–modulated pulses in a thermoviscous fluid." J. Acoustical Society of America, 94 (5), Nov. 1993.

"Small Spheres Lead to Big Ideas." Research News, Science vol. 267, Jan. 20, 1995.

Nico de Jong, "Physical properties and technical aspects of ultrasound contrast agenst", (one page).

excerpt from Ultrasonics: Fundamentals and Applications (1992), pp. 380–393, 363–365.

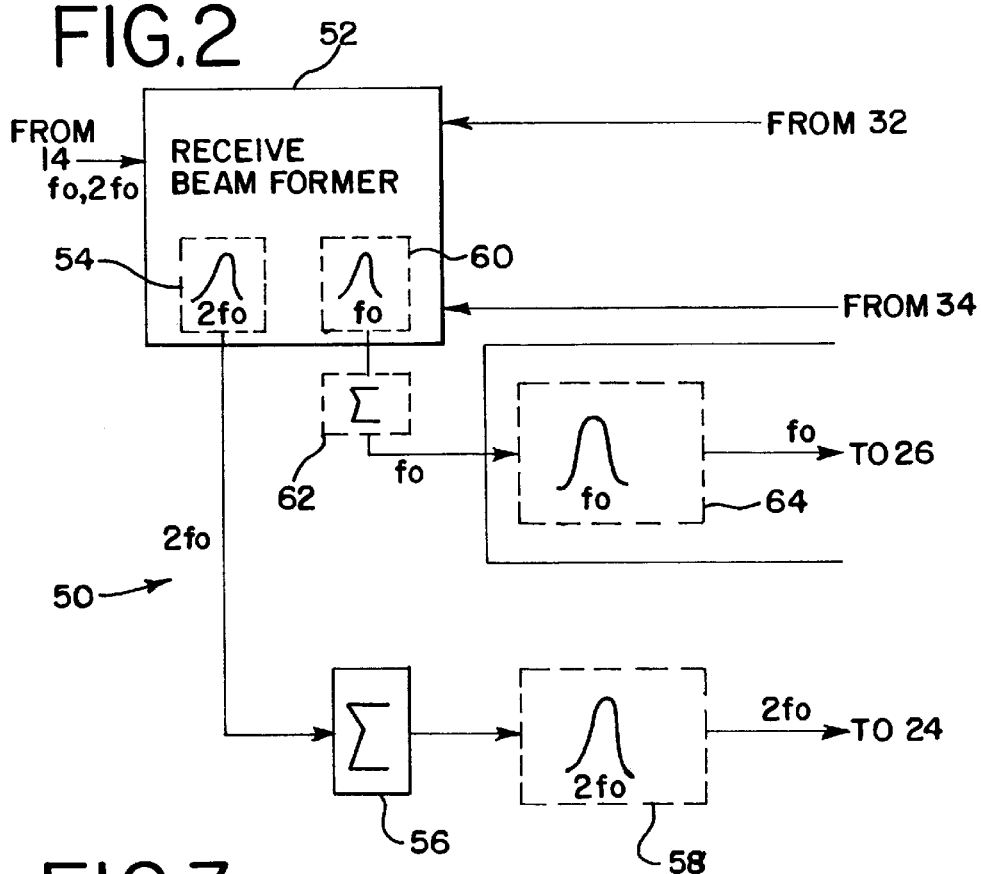
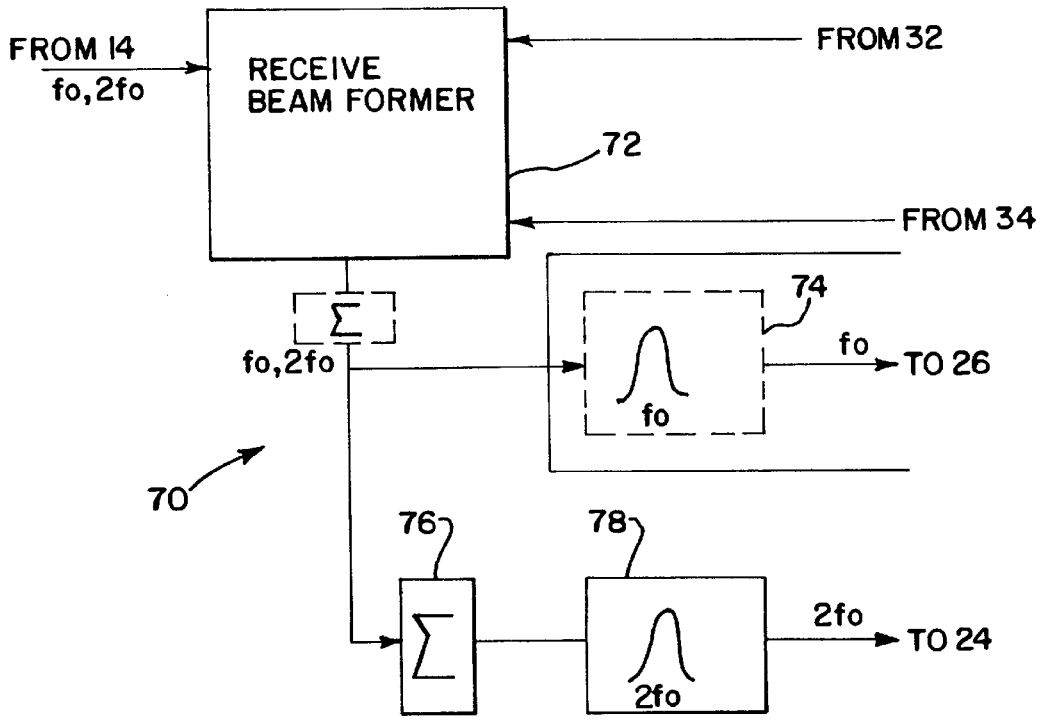

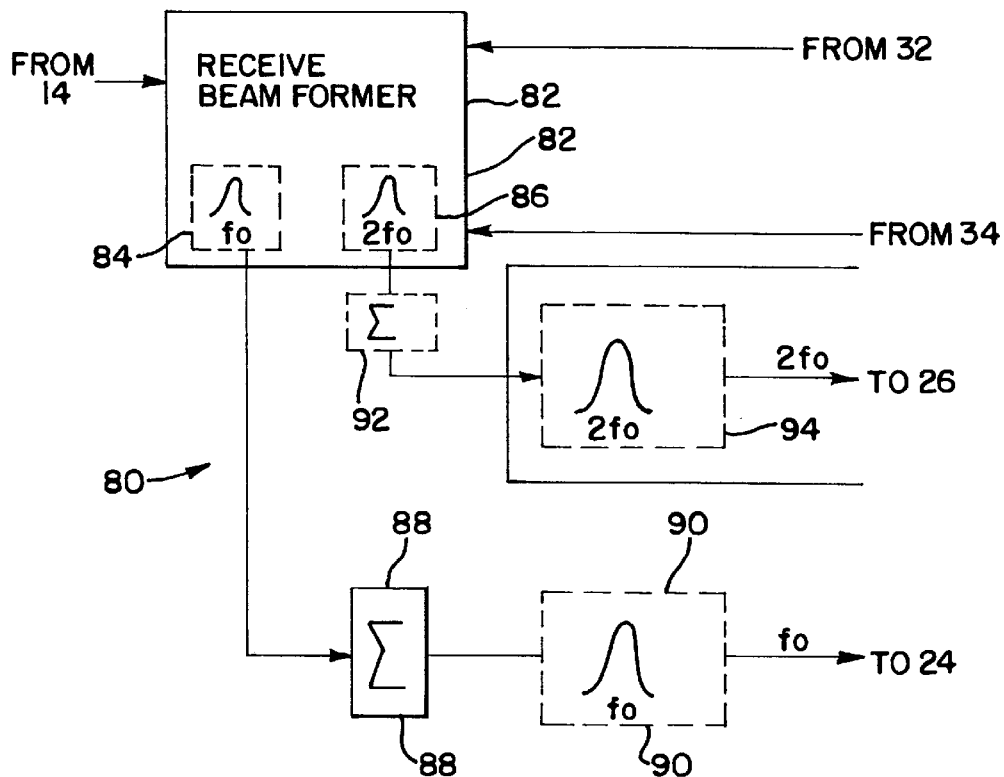
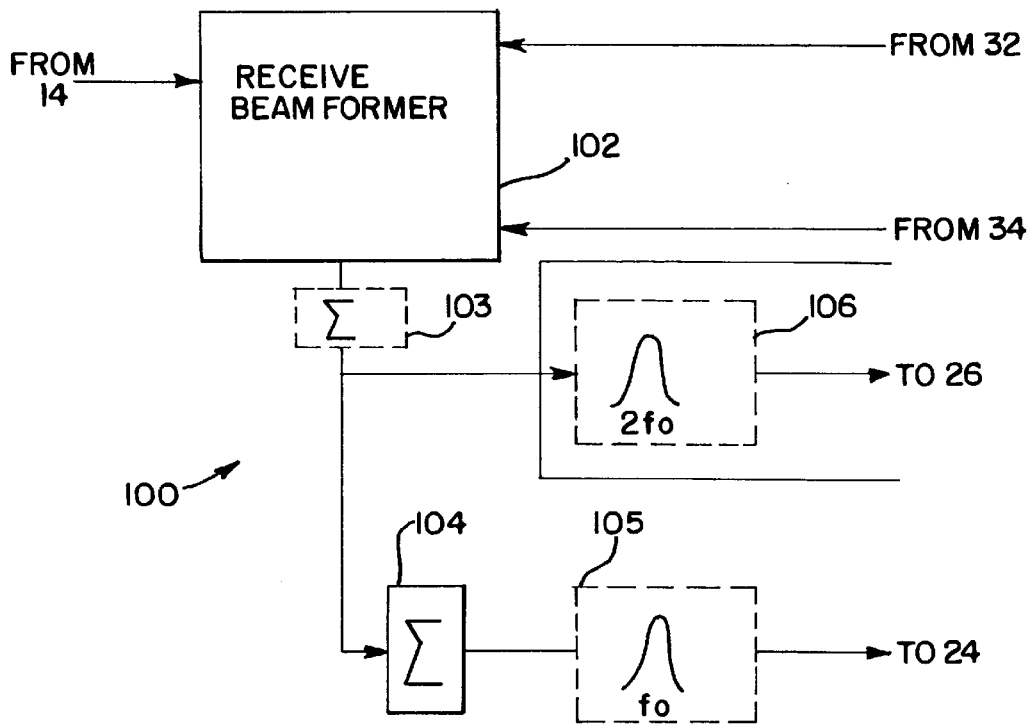

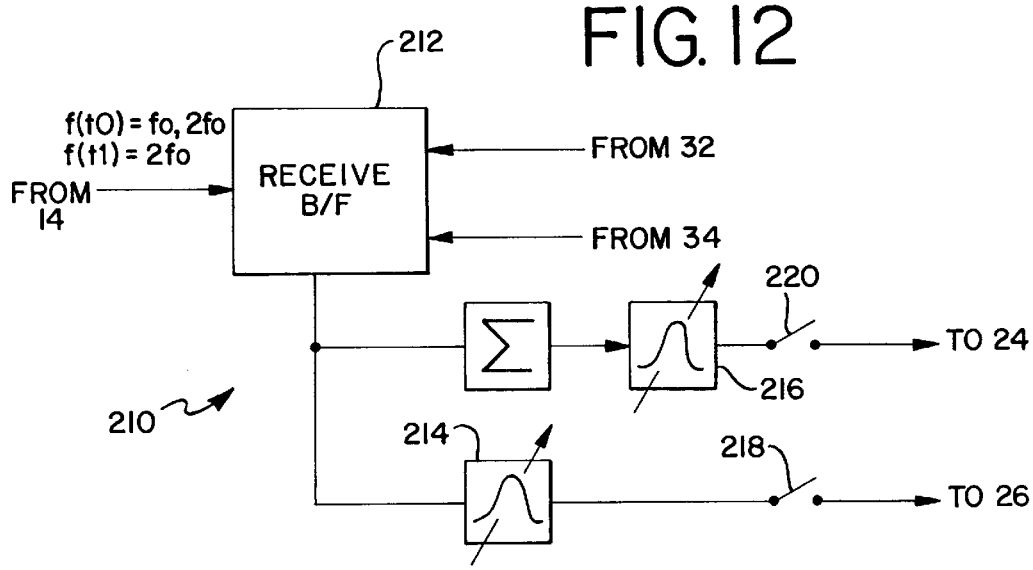
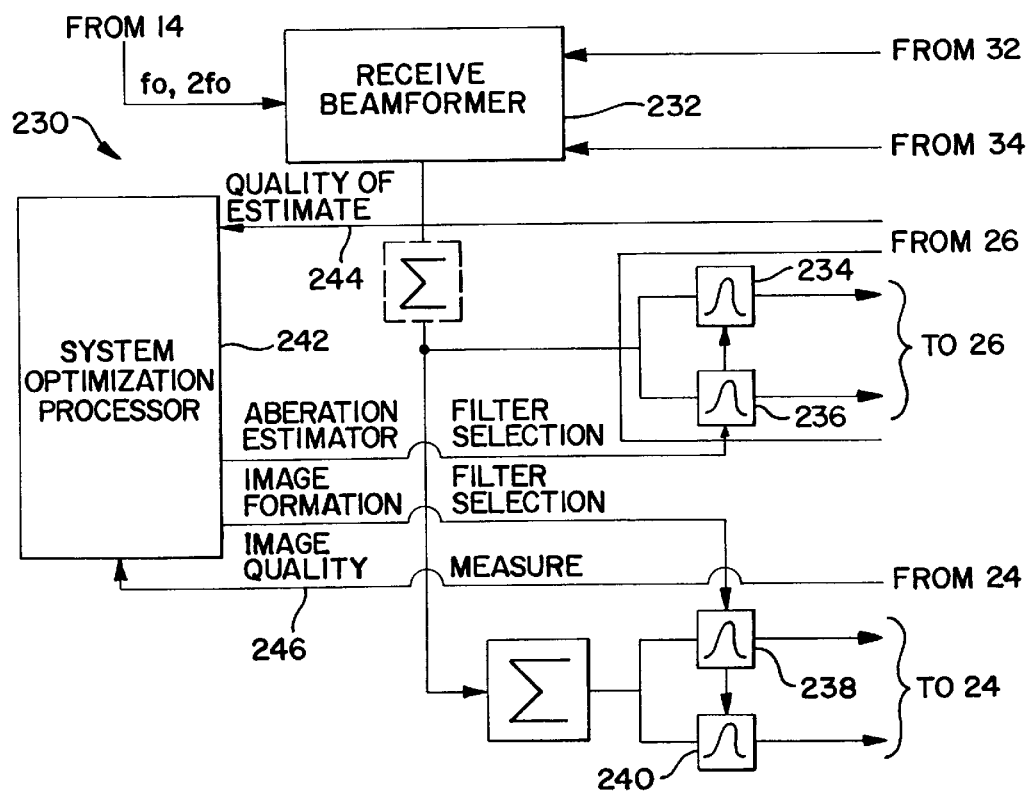

ULTRASONIC IMAGING ABERRATION CORRECTION SYSTEM AND METHOD

This application is a continuation-in-part of U.S. Pat. application Ser. No. 08/940,859, filed Aug. 1, 1997 (abandoned).

BACKGROUND OF THE INVENTION

This invention relates to ultrasonic imaging systems and methods which utilize ultrasound echo information at a harmonic of the fundamental frequency of transmitted ultrasonic energy either for image formation or for aberration correction value estimation.

In an ultrasound imaging system, the velocity of sound is usually assumed constant in tissue in order to calculate time delays in forming acoustic beams from transducer arrays. However, the velocity of ultrasound waves in body tissues varies over a wide range. Therefore, ultrasound waves experience wavefront distortion, which disrupts diffraction patterns and produces image artifacts.

Several approaches have been proposed to correct for sound velocity inhomogeneities in tissue. One approach is to model the sound velocity inhomogeneities as a simple phase screen at or near the face of the transducer. Under this condition, sound velocity inhomogeneities result in time-of-flight errors (i.e., phase aberrations) and the received signal in one channel can be approximated by a time-delayed replica of the signal received by another channel. Therefore, phase aberrations can be estimated (1) by determining the peak position in the cross-correlation of signals received by two adjacent channels or subarrays (S.W. Flax and M. O'Donnell, "Phase aberration correction using signals from point reflectors and diffuse scatterers: basic principles," IEEE Trans. Ultrason., Ferroelect. Freq. Contr., vol. 35, no. 6, pp. 758–767, 1988), or (2) by maximizing speckle brightness via time delay adjustment (L. F. Nock, G. E. Trahey, and S. W. Smith, "Phase aberration correction in medical ultrasound using speckle brightness as a quality factor," J. Acoust. Soc. Am., vol. 85, no. 5, pp. 1819–1833). Another proposed method estimates aberrating delays by utilizing array redundancy in spatial frequency (D. Rachlin, "Direct estimation of aberrating delays in pulse-echo imaging systems," J. Acoust. Soc. Am. vol. 88, no. 1, pp. 191–198, 1990).

The validity of the near field thin phase screen model has been questioned, based on the fact that waveform distortions in addition to time delay errors have been observed. (D. L. Liu and R. C. Waag, "Correction of ultrasonic wavefront distortion using backpropagation and a reference waveform method for time shift compensation," J. Acoust. Soc, Am., vol. 96, no. 2, pp. 649–660, 1994). These waveform distortions have been explained by modeling the acoustic velocity inhomogeneities as distributed throughout the region between the transducer and the target or by putting the phase screen at a distance away from the face of the transducer. Various methods have been proposed to correct for distributed aberrations (or displaced phase screens). They include a back propagation method (Liu, et al., supra), a total least squares (TLS) based approach called PARCA (S. Krishnan, P. C. Li, and M. O'Donnell, "Adaptive compensation of phase and magnitude aberrations," IEEE Trans. Ultrason., Ferroelect. Freq. Contr., vol. 43, no. 1, pp. 44–55, 1996), and a time reversal focusing technique (M. Fink, "Time reversal focusing in ultrasound: basic principles," IEEE Trans. Ultrason., Ferroelect. Freq. Contr., vol. 39, no. 5, pp. 555–566, 1992).

Recently, other alternative approaches have also been developed to correct for distributed aberrations. They include a phase conjugation approach (G. C. Ng, P. D. Freiburger, W. F. Walker, and G. E. Trahey, "A speckle target adaptive imaging technique in the presence of distributed aberrations," IEEE Trans. Ultrason., Ferroelect. Freq. Contr., vol. 44, no. 1, pp. 140–151, 1997), which independently corrects for time delay errors for each frequency component, and an inverse filtering approach (Q. Zhu and B. Steinberg, "Deaberration of incoherent wavefront distortion: an approach toward inverse filtering," IEEE Trans. Ultrason., Ferroelect. Freq. Contr., vol. 44, no. 3, pp. 575–589, 1997), which compensates for both phase and amplitude distortion in the frequency domain.

One major factor that determines the efficacy of all the methods mentioned above is the quality of the transmit beam profile. A good transmit beam profile (narrow mainlobe and low sidelobes) improves both the image quality and the estimation accuracy. It has been shown that harmonically generated transmit beam profiles have lower sidelobes and are less sensitive to the phase aberrations that are present. (T. Christopher, "Finite amplitude distortion-based inhomogeneous pulse echo ultrasonic imaging," IEEE Trans. Ultrason., Ferroelect. Freq. Contr., vol. 44, no. 1, pp. 125–139, 1997).

The above-referenced Christopher article speculates as to aberration correction in a harmonic ultrasonic imaging system, but provides no details as to the structure or operation of any such system.

Wright U.S. Pat. No. 5,570,691, assigned to the assignee of the present invention, discloses one particularly advantageous aberration correction value estimation system in which ultrasonic energy from a single firing or transmit event is used both in the formation of the ultrasonic image and in the calculation of aberration correction values. In this way, the need for separate aberration correction lines or frames can be eliminated.

Johnson U.S. Pat. No. 5,456,257 discloses systems for ultrasonically detecting contrast agents. In one disclosed embodiment signals from collapsing microbubbles included in a contrast agent are used to calculate delay adjustments intended to correct for tissue aberration. Little detail is provided regarding the structure of the disclosed system, and contrast agent is essential for operation of the disclosed system.

SUMMARY OF THE INVENTION

The present invention is defined by the appended claims, and nothing in this section should be taken as a limitation on those claims. By way of general introduction, the present invention relates to aberration correction in ultrasonic imaging systems in which a harmonic of the fundamental transmitted frequency is used for imaging, or for aberration correction, or both. As discussed below, by properly selecting the frequency pass bands of filters used in the image signal path and in the aberration correction signal path, improved systems can be provided with substantial operating advantages. Certain of the embodiments described below calculate aberration correction values concurrently with image formation.

BRIEF DESCRIPTION THE DRAWINGS

FIGS. 2–14 are block diagrams of alternative embodiments of the receive signal processor of FIG. 1.

DETAILED DESCRIPTION OF THE PRESENTLY PREFERRED EMBODIMENTS

General Discussion

Figure 1:
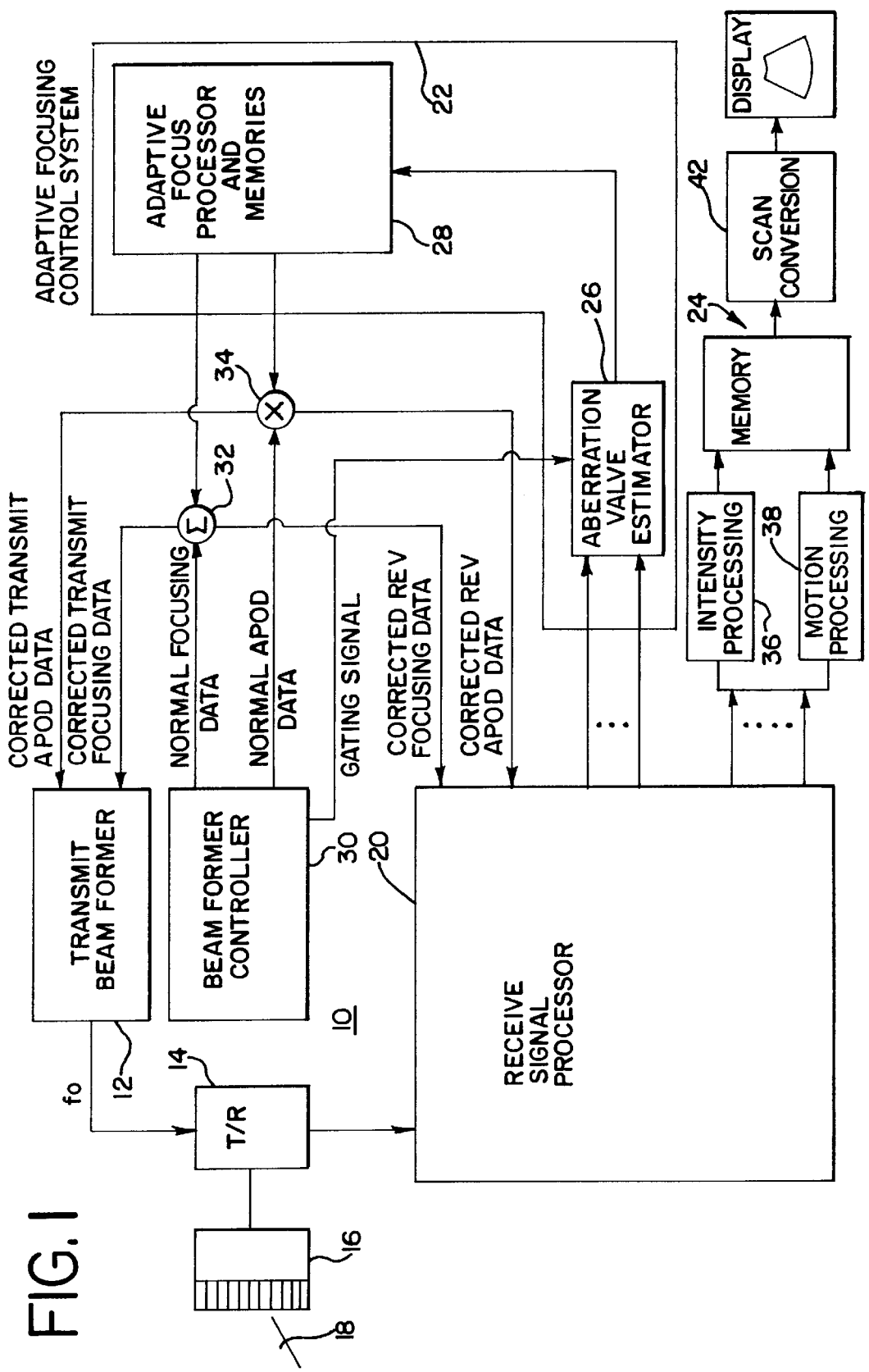
FIG. 1 is a block diagram of an ultrasound imaging system suitable for use with this invention.

As discussed above, several prior-art techniques measure delay differences from transducer element to element (or subarray to subarray, or element to subarray) to obtain aberration correction estimates. These prior-art techniques depend on obtaining a receive signal of measurable amplitude across the face of the transducer array. Specifically, there should not be significant dropouts of signals due to destructive interference (caused by the aberrations) at adjacent transducer elements or subarrays, or the resulting signal to noise ratio will suffer. Lower frequency signals will be less susceptible to such destructive interference, resulting in more uniform amplitudes at adjacent channels at the face of the transducer.

In a typical aberration correction technique, the relative phase received at adjacent elements (or subarrays or subarray/element pairs) is measured and converted to a time delay. Using such a technique, aliasing will occur when the aberration causes a relative delay in the returning wavefront greater than half a wavelength between adjacent transducer elements or subarrays. Specifically, if the aberration causes more than half a wavelength in delay, the aberration correction will be underestimated. This will be less likely to occur at lower frequencies (longer wavelengths), because a greater time delay error can be measured without aliasing using a lower frequency than using a higher frequency.

As a result, more accurate aberration correction estimates can often be obtained using relatively lower receive frequency information.

On the other hand, higher frequency imaging generally provides for better detail and contrast resolution, assuming that adequate penetration can be maintained. As is well known, higher frequencies attenuate in tissue more quickly than lower frequencies. Accordingly, in the absence of aberrations, the use of higher frequencies and the resulting narrower beam profiles will generally result in a better image.

In view of the foregoing, one aspect of the present invention is directed to taking advantage of different properties of different frequency bands or components of the ultrasonic echo information by using different frequency bands for imaging and for aberration correction to improve image quality.

As discussed in detail below, selected embodiments of the invention achieve this objective using tissue harmonic imaging in combination with aberration correction techniques. In tissue harmonic imaging, the ultrasound system images a harmonic response generated by the tissue in response to a transmitted fundamental ultrasound waveform from a transducer. This harmonic response increases as a function of the amplitude of the transmitted waveform. Accordingly, as the transmitted waveform propagates toward the transmit focus, the amplitude of the waveform increases, thus increasing the generation of the harmonic response of the tissue. This results in a generated harmonic frequency transmit beam profile at the transmit focus that has preferred characteristics, and that is less influenced by tissue aberrations, than the transmit beam profile that would have been obtained had the transducer transmitted a signal at the harmonic frequency. Generally, in tissue harmonic imaging no additional non-linear contrast agent is added to the tissue at any time during the ultrasound examination session.

Figure 15:
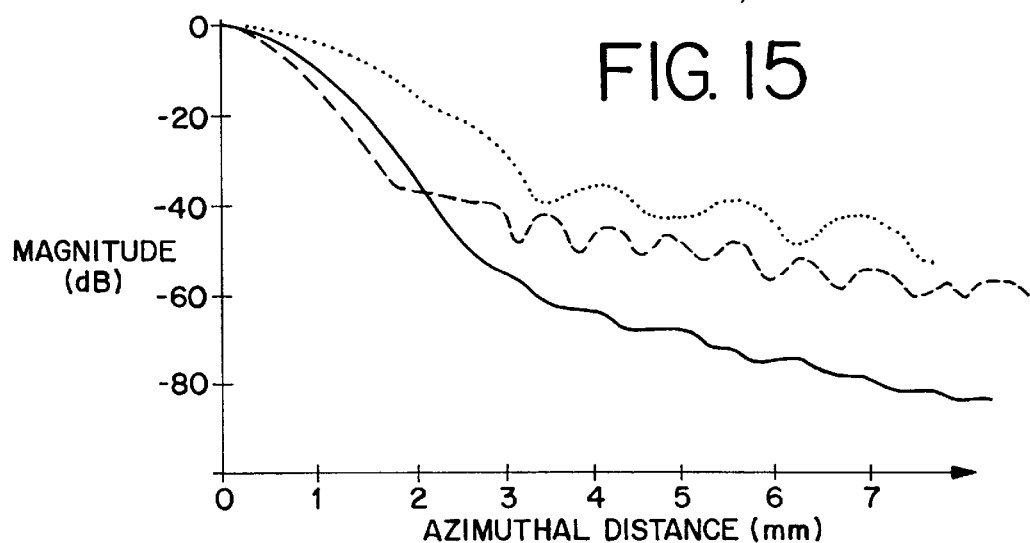
FIG. 15 is a graph showing three alternative beam profiles.

This principle is schematically illustrated in FIG. 15, in which the top, dotted line represents an ideal (absent aberration) transmit beam profile resulting from transmission of a waveform centered at a fundamental frequency, such as a center frequency of 2.5 MHz. The middle, dashed line represents an ideal transmit beam profile resulting from transmission of a waveform centered at a harmonic frequency such as a center frequency of 5 MHz. The lower, solid line represents an ideal transmit beam profile obtained from the harmonically generated frequency band, i.e. transmission of ultrasonic energy at the fundamental frequency and reception of ultrasonic echo information at the harmonic frequency. The solid line shows a profile having the desirable characteristics of a well-formed main lobe (which is narrower than that of the top profile) in combination with low sidelobes.

When aberrations are present, both the fundamental transmit beam profile (from which the harmonic frequencies are generated), and the body generated harmonic beam profile are less affected by aberrations than a transmit beam profile generated by the transducer at the harmonic frequency.

Preferred embodiments of this invention use information from the fundamental and the body generated harmonic beam profiles to create images and to estimate aberration correction values.

In order to obtain the benefit of the body-generated harmonic transmit beam profile described above, it is important to suppress or exclude transmitted ultrasonic energy in the harmonic frequency band. This can be done by shaping the transmit waveform and/or by filtering the output of the transmitter before it is applied to the transducers. Methods and apparatus for achieving a well-formed shaped transmit beam are disclosed in U.S. Pat. Nos. 5,740,128, 5,833,614, and 5,913,823 and application Ser. No. 08/893,271. Resulting transmit waveforms will be referred to herein as "shaped fundamental" waveforms. In these shaped fundamental waveforms, the second harmonic component is suppressed by at least 20 dB throughout a bandwidth of 10% around the second harmonic frequency (i.e., if the second harmonic is at 5 MHz, then from 4.75 to 5.25 MHz the signal is suppressed by 20 dB or more with respect to the signal level at the fundamental frequency). The second harmonic is preferably suppressed by at least 35 dB throughout a bandwidth of 15% around the harmonic frequency, and more preferably is suppressed by at least 45 dB throughout a bandwidth of 20% around the harmonic frequency. Most preferably, the second harmonic is suppressed by at least 55 dB throughout a bandwidth of 25% around the harmonic frequency.

FIG. 1 shows a block diagram of an ultrasonic imaging system 10 that can be used to implement this invention. The system 10 includes a transmit beamformer 12 that applies transmit waveforms via a transmit/receive switch 14 to a transducer array 16. The transducer array 16 operates as a phased array, and the transmit beamformer 12 times the transmit waveforms as appropriate to focus transmitted ultrasonic energy from the transducer array 16 at a desired direction and range.

The transmit beamformer 12 can be implemented in any suitable manner including either analog or digital beamformers. The presently preferred transmit beamformer 12 takes the form described in U.S. patent application Ser. No. 08/673,410, filed Jul. 15, 1996, assigned to the assignee of the present invention. The transmit beamformer 12 can also take the form of any of the transmit beamformers described in the above-identified U.S. Pat. Nos. 5,740,128, 5,833,614, and 5,913,823 and application Ser. No. 08/893,271.

The transducer array 16 generates ultrasonic energy that is transmitted into a target 18, typically a tissue of the subject. In alternative embodiments, the transducer array 16 may be a one dimensional, one and a half dimensional or two dimensional array, as appropriate for the application. The target 18 may optionally include a non-linear contrast agent added to increase the harmonic response of the tissue. However, in many applications it is preferable to avoid the use of added non-linear contrast agent, and to rely on tissue harmonic imaging as described above, in which the body tissue itself generates ultrasonic energy at a harmonic of the fundamental frequency transmitted by the transducer array 16 and no additional non-linear contrast agent is introduced into the patient at any time during the ultrasound examination session. Such tissue harmonic imaging can be used in all of the specific embodiments described below.

Ultrasonic echo information received by the transducer array 16 is routed by the switch 14 to a receive signal processor 20. The receive signal processor 20 typically includes a receive beamformer and filters as described in detail below. The receive signal processor 20 applies output signals to an adaptive focusing control system 22 and to an image processor 24.

As shown in FIG. 1, the adaptive focusing control system 22 includes an aberration correction value estimator 26 and an adaptive focus processor 28. The estimator 26 and the processor 28 preferably take the form described in U.S. Pat. No. 5,570,691, assigned to the assignee of the present invention. Generally speaking, in this embodiment the aberration correction value estimator 26 estimates aberration correction values both in terms of focusing phase or delay and amplitude. The processor 28 stores the aberration correction values determined by the estimator 26 and uses these stored values to correct both focusing and amplitude aberrations associated with both the transmitted and the received ultrasonic echo information. In this embodiment, correction values for focusing phase or delay are determined by cross-correlating signals from adjacent regions of the transducer array 16.

The aberration correction value estimator 26 can use partial summation signals from subarrays of transducer elements in calculating aberration correction values. When such subarrays are used, the signals from two or more adjacent transducer elements are summed to form subarray sums. The signals being summed have already been adjusted by the normal focusing delays and apodization values by the receive beamformer and have also been adjusted by previous aberration delay estimates and apodization correction values from the apodization focus processor 28. (As used herein "normal" as applied to focusing delays and apodization values means values not taking aberrations into account.) In the aberration correction value estimator 26 the subarray sums are processed to determine the residual error (whether from delay, apodization, or both) across all subarrays. While it is preferred to use subarrays to reduce hardware complexity, in alternative embodiments the aberration correction value estimator 26 may respond to individual transducer channels rather than subarrays.

In addition to measuring phase error of the subarray sum signals, the aberration correction value estimator 26 also measures the amplitude of the signals in order to determine the amplitude variations between various elements or subarrays in the array. At one or more specific ranges, the digital signal values are averaged to determine an average signal level over a few cycles. The magnitude of the signals is used in this calculation to eliminate cancellation due to positive and negative phases.

In particular, the system 10 includes a beamformer controller 30 that generates normal focusing data and apodization data as shown. The normal focusing data is applied to a summer 32 that also receives focusing aberration correction values from the processor 28. The normal focusing data supplied by the beamformer controller 30 is determined by geometrical considerations assuming no tissue aberration. The output of the summer 32 combines normal focusing data appropriate for the selected acoustic line as well as focusing aberration correction values as determined by the estimator 26 and the processor 28. The sum is applied as corrected transmit focusing data to the transmit beamformer 12 and as corrected receive focusing data to the receive signal processor 20.

Similarly, the system 10 includes a multiplier 34 that receives input signals both from the beamformer controller (normal apodization data) and from the processor 28 (amplitude aberration correction values). The product of these two inputs is supplied as corrected transmit apodization data to the transmit beamformer 12 and as corrected receive apodization data to the receive signal processor 20.

The aberration correction value estimator 26 may operate for all scan lines or for only a subset of scan lines and may operate at one range (typically the transmit focus) or multiple ranges. If aberration correction values are derived from multiple lines and/or ranges, the resulting data is preferably stored in a table which is used subsequently to determine aberration correction values by means of interpolation for example. See for example, U.S. Pat. No. 5,570,691, assigned to the assignee of the present invention. Simpler systems in which aberration correction values are only calculated for as little as one range and one acoustic line are also allowed for in this invention. As part of its operation, the adaptive focus processor 28 may interpolate focusing and apodization correction values detected for specific transducer subarrays to determine correction values to be applied to individual array channels.

The aberration correction value estimator preferably responds to a gating signal from the beamformer controller 30 such that the aberration correction value estimator 26 and the image processor 24 are both responsive to ultrasonic echo information associated with the same transmit event or firing of the transducer array 16. Preferably, the aberration correction value estimator 26 operates only on a predetermined range of the received ultrasonic echo information. This is accomplished by a gating signal as described in U.S. Pat. No. 5,570,691. A suitable embodiment for the aberration correction value estimator is described in U.S. Pat. No. 5,570,691 at columns 21–22. See the aberration value estimator G-502 of FIG. 6 of that patent. Gating of the estimator is shown in FIGS. 4 and 5 (see Reference Nos. 550 and 572, 574, respectively). Other aberration value correction techniques may be used with this invention.

In the preferred embodiment of FIG. 1 the normal and corrected delay and apodization values are combined by the summer 32 and the multiplier 34 prior to being sent to the transmit beamformer 12 and the receive signal processor 20. In alternative embodiments the combining can take place as part of the beam formation process.

As explained above, the receive signal processor 20 also supplies beamformed signals to the image processor 24. The image processor 24 can take any suitable form, and can be constructed as an analog, digital or hybrid system. The image processor 24 preferably includes brightness or intensity processing circuitry 36 and motion processing circuitry 38. The elements 36, 38 can take any suitable form, and if desired the motion processing circuitry 38 may be deleted. The processing circuitry 36 can be implemented by any known or later developed type of image processing that involves displaying the information with brightness representing intensity, such as known B-mode and/or M-mode ultrasound image processing. This type of image is typically but not always displayed as a gray scale. The processing circuitry 38 may include any desired type of motion processing such as color Doppler or time shift information processing, and is typically but not always displayed in color. Output signals from the elements 36, 38 are stored in a memory 40 prior to scan conversion in a scan converter 42. The scan converted output of the image processor 24 is applied to a conventional display 44. The brightness processing circuitry 36 and the motion processing circuitry may be used in combination for a single image.

As explained below, the receive signal processor 28 can be adapted to supply the desired frequency components of the received signal to the aberration correction value estimator 26 and to the image processor 24. In one preferred embodiment, a shaped fundamental transmit waveform is transmitted (centered at the fundamental frequency $f_0$) and the return signal is selectively received at a harmonic frequency band (centered at $2f_0$) and used to form an ultrasound image. Ultrasonic echo information may also be optionally selectively received at the fundamental frequency band (centered at $f_0$), and this information may also be optionally used in the formation of the image. As discussed below, in certain circumstances it may be desirable to combine the fundamental and harmonic components of the echo information in the image processor 24.

Similarly, in various embodiments, aberration correction values are estimated from information obtained from the fundamental frequency component, the harmonic frequency component, or both. Depending upon the application, it may be preferable to allow great flexibility in the filtering characteristics of the receive signal processor 20. Alternately, simpler but less flexible implementations are possible in which fixed filters are provided in the two signal paths provided by the receive signal processor 20 for the adaptive focusing control system 22 and the image processor 24. For example, in selected ones of the preferred embodiments discussed below a harmonic filter is used in the signal path for the image processor 24 and a fundamental filter is used in the signal path for the aberration correction value estimator 26.

The aberration estimation can be determined using a transmit firing dedicated to the aberration estimate, and not used for creating the image. Alternatively, a wide band signal can be received, and the bandwidth of the receive signal filtered appropriately for the image and aberration correction signal paths. For example, the entire bandwidth of the receive signal or the fundamental band of the receive signal can be used for image formation, while only the fundamental or harmonic component of the receive signal can be used for aberration value estimation.

Specific Embodiments

The receive signal processor 20 can take many forms, and the following sections discuss selected embodiments. In FIGS. 2–14 the illustrated receive signal processors have been designed to function within the ultrasonic imaging system 10 of FIG. 1, receiving input signals from the switch 14, the summer 32 and the multiplier 34, and providing output signals to the adaptive aberration value estimator 26 and the image processor 24.

Turning now to FIG. 2, the receive signal processor 50 includes a receive beamformer 52. The receive beamformer 52 is preferably a digital beamformer, but it may be implemented as an analog beamformer if desired. Ultrasonic echo information from the transducer array 16 and the switch 14 passes through high voltage clamping circuits for receiver protection and preamplifiers. These preamplified signals are then passed through time varying amplifiers prior to conversion to digital quantities in an analog to digital converter. The receive beamformer 52 typically operates with base band signals in the form of in phase and quadrature (I, Q) quantities. The focusing delay profile is dynamically updated as the focal depth evolves for signals arriving from progressively deeper regions of the target.

The receive beamformer 52 receives aberration corrected delays and apodization values, which may if desired change dynamically (i.e. delays associated with aberration correction which may change as a function of elapsed time from the start of the transmit event are added to dynamically changing focus delays). In this way, near ideal focal delays are applied to obtain near perfect focusing, despite the presence of aberrating tissue delays. Amplitude correction values are also applied to the receive signals by means of scaling multipliers. Alternately, correcting amplitude factors may be applied by means of the controlled gain amplifiers, in which case the gain is determined by an applied voltage derived from the amplitude correction values.

In this embodiment the receive beamformer 52 is a multiple beam beamformer that simultaneously forms appropriately delayed outputs for two respective beams from a single transmit event. The first of these beams is demodulated with a frequency $2f_0$ (schematically illustrated by the filter 54) and then applied via a summer 56 which sums all channels to a filter 58. In this case the filter 58 is a baseband filter that passes signals energy that was originally centered at the harmonic frequency $2f_0$ prior to demodulation. The beamformed receive signal in the harmonic frequency band is applied as an input to the image processor 24 of FIG. 1.

The second beam formed by the receive beamformer 52 is demodulated with the fundamental frequency $f_0$, schematically indicated by the filter 60. The time delayed signals from two or more adjacent transducer elements are summed in a partial summer 62 and applied as an input to a low pass filter 64 which passes signal energy that was originally centered at the fundamental frequency $f_0$ prior to demodulation. This demodulated, filtered, partially summed signal obtained from a receive signal at the frequency band centered at the fundamental $f_0$ is applied as an input to the aberration correction value estimator 26 of FIG. 1.

In the embodiment of FIG. 2 the two beams formed by the receive beamformer 52 are focused using both time and phase adjustments. The least significant bits of the time delay are converted to phase adjustments. While time adjustments are independent of frequency, phase adjustments are not. Because the receive beamformer 52 produces two beams, each can be optimally focused using phase adjustments as appropriate for the harmonic and the fundamental receive information, respectively.

The filters in the receive beamformer 52 can be regarded as coarse adjustments, and the filters 58, 64 may be regarded as fine adjustments to signal quality. If desired, the filter 54 or the filter 58 can be deleted. Similarly, if desired, the filter 60 or the filter 64 can be deleted. As explained above, if the aberration correction value estimator is intended to function on individual transducer channels the partial summer 62 can also be eliminated. In another embodiment related to that of FIG. 2, the aberration correction value estimator is responsive to the entire unfiltered broadband receive signal, which is made up primarily of ultrasonic echo information in the fundamental pass band.

In receive signal processors such as the processor 50, a filter such as filter 58 in the imaging path can be implemented as the baseband filter, such as the filter described in U.S. patent application Ser. No. 08/434,160, filed May 2, 1995, and assigned to the assignee of this invention. Since the signal applied to the filter 58, 64 is downshifted to baseband (i.e. DC) in the receive beamforming process, the fine adjustment filter 58, 64 is typically implemented as a low pass filter about DC.

The embodiment of FIG. 2 is particularly advantageous in situations where aliasing or dropout problems are encountered in the event aberration correction estimation is attempted at the harmonic. It is anticipated that the embodiment of FIG. 2 will be well suited for B-mode or M-mode imaging.

The embodiment of FIG. 2 is also anticipated to be well adapted for calculating error correction values when aberration correction is needed in regions of relatively greater depths. Since lower frequencies are less attenuated by body tissues than higher frequencies, a better signal to noise ratio (SNR) will be obtained in such circumstances if the fundamental frequency component rather than the harmonic frequency component is used to calculate aberration corrections. In particular, there is a significant difference in the SNR level in the correction and imaging paths due to the facts that SNR varies as the square root of the number of channels, and the number of channels is substantially smaller in the correction path than the imaging path. For this reason, the quality of the information applied to the aberration correction value estimator is not as high as that applied to the image processor, and it is therefore particularly advantageous to use the fundamental component of the ultrasonic echo information for aberration correction.

FIG. 3 shows a block diagram of a receive signal processor 70 that also applies received ultrasonic echo information in the fundamental pass band to the aberration correction value estimator, and received ultrasonic echo information in the harmonic pass band to the image processor. In this case the receive signal processor 70 includes a receive beam-former 72 that operates as described above except that it produces a single output signal, a wide band signal including both the fundamental and harmonic frequency components. This wide band signal is optionally partially summed to form a subarray summation signal which is applied to an optional filter 74 designed to pass the fundamental component near $f_0$ and to block the harmonic component near $2f_0$. The output of the optional filter 74 is applied to the aberration correction value estimator 26 of FIG. 1. The partial summation signals are applied to a summer 76, and the output of the summer 76 is applied to a filter 78 designed to pass the harmonic component near $2f_0$ and to block the fundamental component near $f_0$. As explained above, the filter 74 may be deleted if desired. As in the embodiment of FIG. 1, aberration corrections are estimated based on the fundamental component of the ultrasonic echo information, while the image is formed based on the harmonic component of the ultrasonic echo information.

FIGS. 4 and 5 relate to receive signal processors 80, 90, respectively, which apply ultrasonic echo information from the harmonic frequency band ($2f_0$) to the aberration correction value estimator 26 of FIG. 1 and ultrasonic echo information from the fundamental frequency band ($f_0$) to the image processor 24 of FIG. 1. The receive signal processor 80 of FIG. 4 includes a dual beam receive beamformer 82 that generates two receive beams in response to each transmit event. The first beam is demodulated to emphasize ultrasound echo information near the fundamental frequency $f_0$ (schematically indicated by the filter 84), and the second receive beam is demodulated to emphasize received ultrasonic echo information at the harmonic (schematically indicated by the filter 86). The first receive beam demodulated at the fundamental frequency $f_0$ is applied to a summer 88 and via a filter 90 that suppresses the harmonic component applied to the image processor. The second receive beam is applied via an optional partial summer 92 and a filter 94 that suppresses the fundamental component applied to the aberration correction value estimator. As before, one or both of the filters 86, 94 may be deleted and one or both of the filters 84, 90 may be deleted. Also, the partial summer 92 is not required in all applications. The receive beamformer 82 of FIG. 4 provides many of the advantages of the dual beam receive beamformer 52 of FIG. 2.

The receive signal processor 100 of FIG. 5 uses a receive beam-former 102 that generates a single output delayed and amplitude adjusted as described above. An optional partial summer 103 is included, and the output of the partial summer 103 (if present) is supplied via a summer 104 and a fundamental filter 105 as an input to the image processor. Partially summed signals from the partial summer 103 (if present) are applied via a harmonic filter 106 as an input to the aberration correction value estimator.

It is anticipated that the embodiments of FIGS. 4 and 5 will be well suited for color Doppler (F-mode) applications, where it is advantageous to use lower frequencies for imaging and higher frequencies for calculating aberration corrections. The use of low frequencies for imaging in color Doppler applications is important because sensitivity is a greater issue. Received fundamental Doppler signals are at a much lower signal level than received fundamental B-mode imaging signals, e.g. 40 dB lower at a given fundamental frequency. Because of greater attenuation at higher frequencies, the lower frequencies will be of larger amplitude and therefore easier to detect, providing better information for imaging. On the other hand, harmonic signals used for calculating aberration corrections, which are the sum of one or a small number of channels, are about 40 dB below the B-mode imaging signal level. Thus, harmonic correction signals are comparable to the signal level for color Doppler imaging. If the SNR is adequate for color processing the fundamental frequency component, it should also be adequate for aberration correcting the harmonic frequency component. If the SNR is adequate, it is preferred to perform aberration correction calculations using the harmonic component, because the harmonically generated transmit beam profile is well formed, and has lower sidelobes, giving a more accurate result.

The harmonic component is preferred for aberration correction in circumstances where aliasing is not a problem, and the signal to noise ratio of the harmonic beam is above a threshold value. Where circumstances permit, it is generally preferred to use the harmonic component for aberration calculations.

The composite, or overall beam profile (sometimes referred as the point spread function) determines the sensitivity of an ultrasound system. The composite beam profile can be approximated by multiplying the transmit beam profile and the receive beam profile. For each subarray of the transducer array, the receive beam profile is rather unfocused, since it is created from a relatively small number of channels (1 to 4 in the preferred embodiment, although a larger number of channels can be used per subarray in alternative embodiments). On the other hand, a much larger number of elements are used on transmit, with the result that the transmit beam profile is much more focused (localized). For this reason, when the transmit and receive beam profiles are multiplied together to create the composite profile of a subarray signal, the composite profile will look very much like the transmit beam profile. As discussed above in conjunction with FIG. 15, the harmonically generated transmit beam profile is desirable to use whenever possible, because it has a well-formed main lobe and small side lobes. Accordingly, it should give more accurate results in calculating aberration correction values, providing that there is no excessive aliasing and that the signal to noise ratio is adequate, i.e. that the signal has not been overly diminished due to attenuation.

Figure 6:
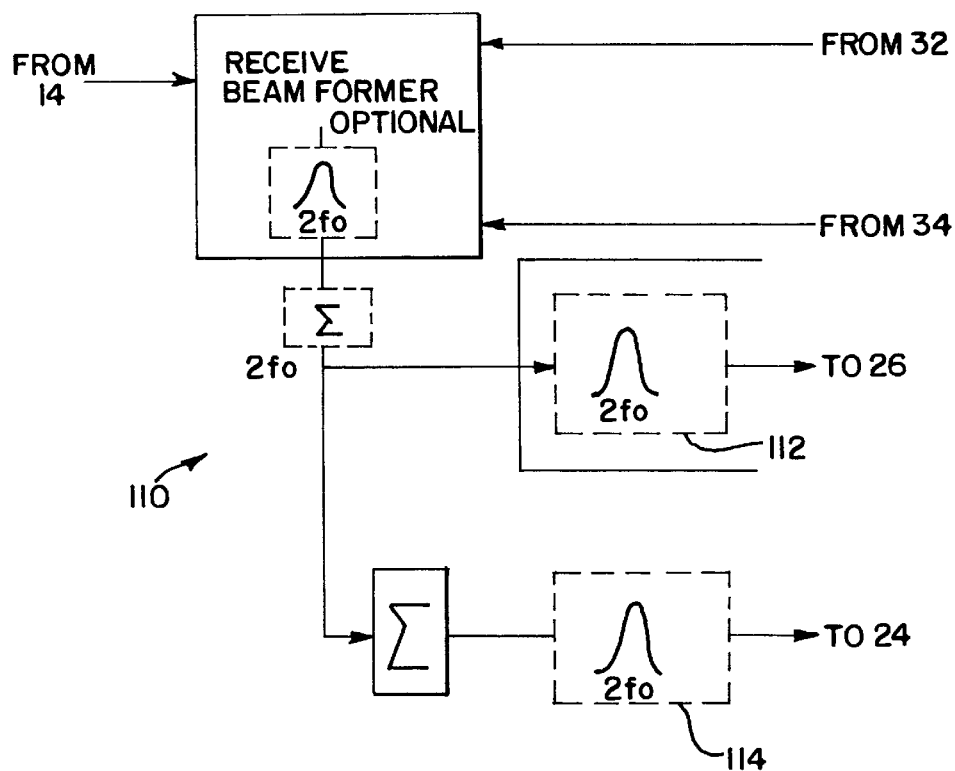
Figure 7:
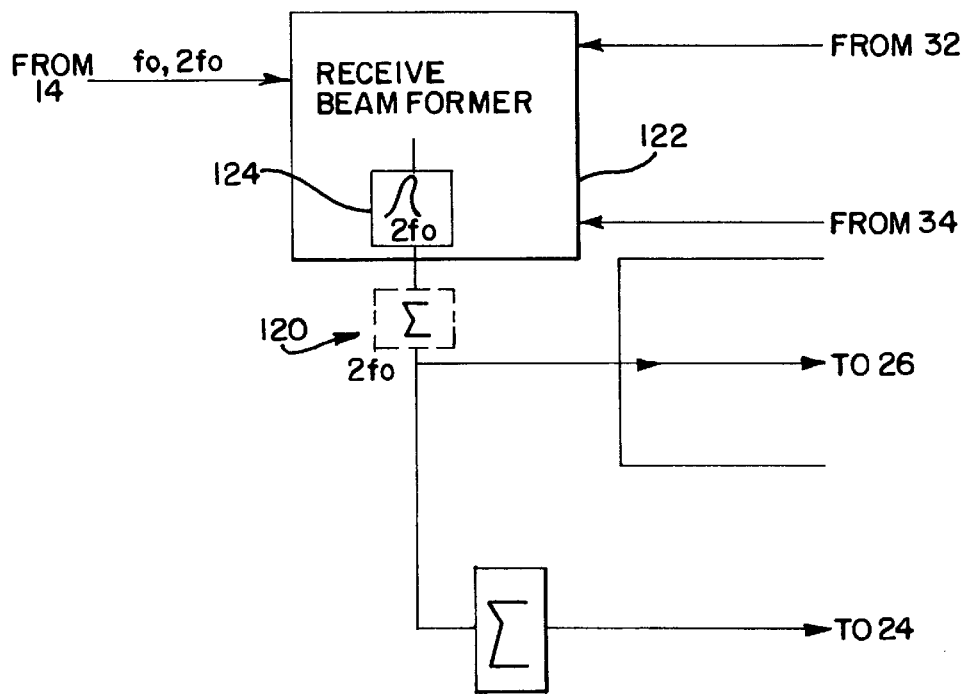

FIGS. 6 and 7 relate to receive signal processors 110, 120, respectively, that apply harmonic signals to both the aberration correction value estimator and the image processor. The receive signal processor 110 of FIG. 6 is similar to the processor 90 discussed above, except that both of the filters 112, 114 are harmonic filters that pass received ultrasonic echo information at the harmonic rather than the fundamental ($2f_0$ rather than $f_0$ in this example). The receive signal processor 120 of FIG. 7 achieves the same result with a receive beamformer 122 that demodulates the receive signals from the transducer array to emphasize the harmonic $2f_0$ (schematically indicated by the filter 124). As described above, echo information from a single transmit event is preferably applied both to the imaging and the correction data paths, such that calculation of aberration correction values proceeds concurrently with image formation.

Though the filters 112, 114 are shown as harmonic filters in FIG. 6, they do not have to be precisely the same filters. In fact, in one particularly preferred embodiment the filter 114 for the image processor passes as wide a bandwidth as possible about the second harmonic while still rejecting the fundamental frequency band, and the filter 112 passes a narrower pass band (possibly as much as a factor of two or more narrower than that used in the filter 114). This narrower bandwidth may be beneficial in the conversion from phase delay to time delay in the event the aberration correction value estimator 26 uses a narrow band correlation technique (i.e. measuring phase difference between adjacent elements or subarrays) to estimate time delays.

Figure 8:
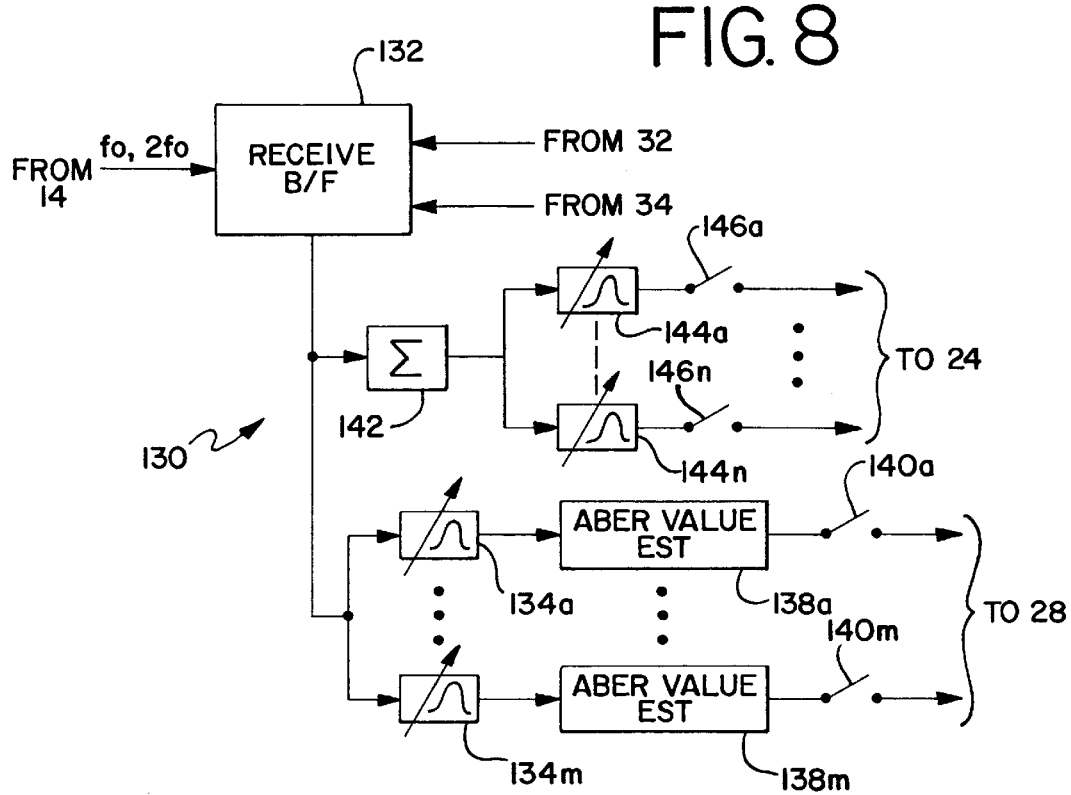

FIGS. 8 through 12 relate to other embodiments of the receive signal processor of FIG. 1 that are particularly well adapted to allow ready adjustment of the frequency bandpass used for the correction path and the imaging path. As shown in FIG. 8, the receive signal processor 130 includes a single beam receive beamformer 132 that provides at its output a wideband receive signal that includes both the fundamental and the harmonic components. This output signal of the receive beamformer 132 is applied in parallel to m different filters 134a–134m. Each of the filters 134a–134m is adjustable, and the pass band of the respective filters can be controlled by respective control inputs. The outputs of the various filters 134a–134m are applied to separate aberration correction value estimators 138a–138m. Each aberration correction value estimator 138a–138m generates a respective set of aberration correction values based on the respective filtered input signal. Selected ones of these aberration correction values are further processed, as controlled by the switches 140a–140m. Though not shown in FIG. 8, a partial summation as described above can be provided in the correction path.

As shown in FIG. 8, the imaging path includes a summer 142 that provides summed, beamformed signals as inputs to a plurality of imaging filters 144a–144n. Each of the imaging filters 144a–144n is separately adjustable as to pass band by a respective control input, and the outputs of selected ones of the filters 144a–144n are passed to the image processor 24, gated by switches 146a–146n. This arrangement allows great flexibility in choosing one or more signals of respective frequency bands for aberration correction value estimation and for imaging. For example, the image processor 24 can combine the signals from multiple frequency bands in any desired manner. If desired, the receive beamformer 132 can be of the type that provides multiple receive beams, demodulated at respective center frequencies.

Figure 9:
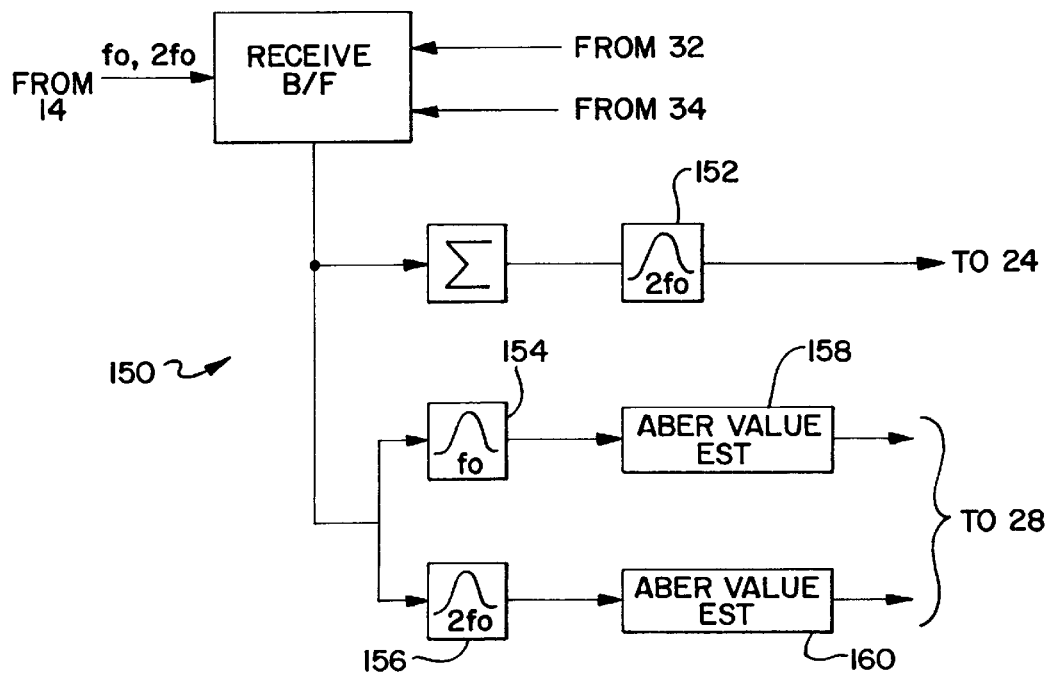

The receive signal processor 150 of FIG. 9 supplies the harmonic component of the ultrasound echo information to the image processor, as filtered by the pass band filter 152. The correction path in the receive signal processor 150 includes two separate pass band filters 154, 156 connected in parallel. In this embodiment the filter 154 is centered at the fundamental pass band, and the filter 156 is centered at the harmonic pass band. The outputs of these filters 154, 156 are applied to separate respective aberration correction value estimators 158, 160. The embodiment of FIG. 9 supports imaging at the harmonic and aberration correction using a combination of harmonic and fundamental components of the echo information. It is anticipated that it may be particularly desirable to combine the fundamental frequency component (which provides excellent penetration and reduced signal to noise problems) with the harmonic component for improved accuracy because of the smaller transmit beam profile. For example, an average, a weighted average or a thresholded average of the two components may be used.

Figure 10:
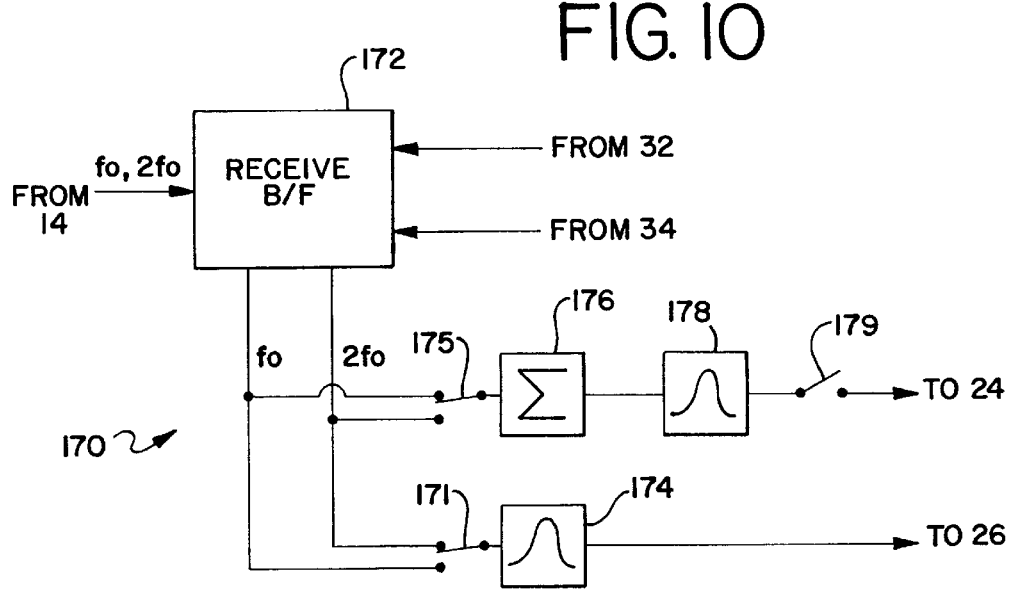

FIG. 10 shows another receive signal processor 170 that includes a dual beam receive beamformer 172. The two beams are demodulated with center frequencies at the fundamental and second harmonic, respectively. Ultrasound echo information from either of the two receive beams generated by the receive beamformer 172 can be routed to the correction path via the switch 171 and the filter 174. Similarly, ultrasonic echo information in either of the two receive beams can be routed via the switch 175, the summer 176, the filter 178 and the switch 179 to the image processor. By properly controlling the switches of FIG. 10 either one of the two receive beams can be used as a source of ultrasound echo information for either of the two signal paths.

Figure 11:
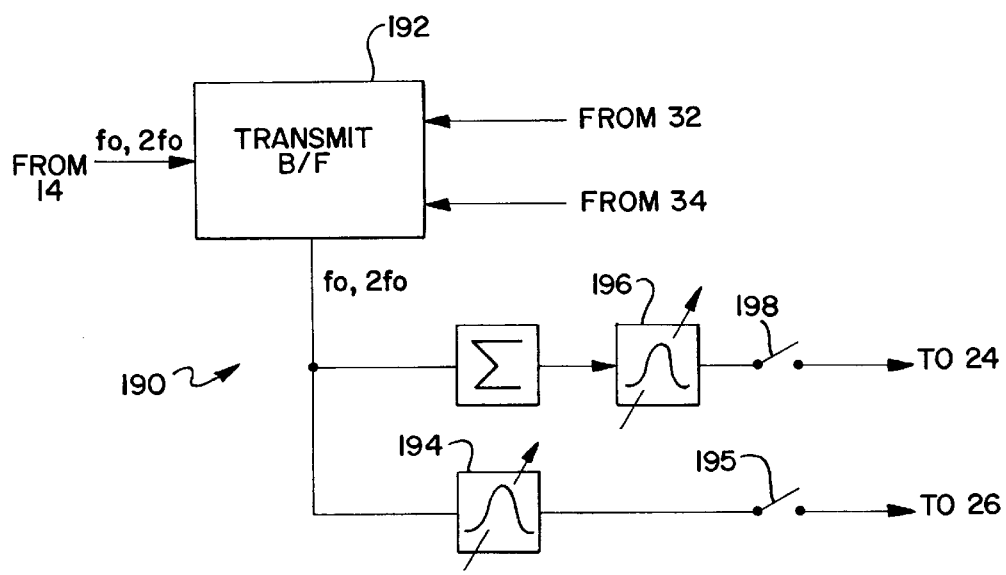

FIG. 11 shows another receive signal processor 190 that includes a single beam receive beamformer 192 that is demodulated in a broadband manner such that both fundamental and harmonic components appear at the output of the receive beamformer. The correction signal path includes an adjustable filter 194 and a switch 195. The image signal path includes an adjustable filter 196 and a switch 198. The receive signal processor 190 of FIG. 11 can be used in a time multiplexed fashion. By properly controlling the adjustable filters and the switches the ultrasound echo information can be routed differently for different firings of the transducer.

The processors of FIGS. 10 and 11 may be operated in a sequential mode in which the signals for aberration correction estimation are first filtered with one filter configuration and the resulting aberration correction values stored in correction value memory, and then aberration correction values are created in a second transducer firing from a signal filtered with a different filter configuration, or an all pass filter (i.e. no filter). Once the second aberration correction value is obtained, these two estimates (both stored in the correction value memory) are passed to the adaptive focus processor 28 of FIG. 1, which analyzes the results of the estimates of the aberration correction value. The advantage of using more than one estimate of aberration correction value is that a more stable and reliable result may be obtained. In one version, only aberration correction values derived from the fundamental component of the received signal are analyzed.

As another example, the transducer may be fired at a fundamental frequency band and then ultrasound echo information may be selectively received from this first firing at a harmonic frequency band and used for image processing. Then a second ultrasound firing can be performed at the fundamental frequency band, and received ultrasonic information from the second firing in the fundamental frequency band can be used to determine aberration correction values. Alternatively the harmonic frequency band from the second firing or both the harmonic and fundamental frequency bands from the second firing can be used to determine aberration correction values. It is not essential in all cases that fundamental and harmonic frequency bands be used, and in an alternative embodiment a lower frequency band can be transmitted in the first and second firings. A higher frequency band can be used for at least a portion of the image and either the higher, the lower, or both frequency bands can be used in the correction path for the calculation of aberration correction values.

FIG. 12 shows another receive signal processor 210 that is designed to operate with consecutive firings of the transducer at different frequency bands. The receive signal processor 210 includes a receive beamformer 212 that supplies receive signals to a correction path via an adjustable filter 214 and to an imaging path via an adjustable filter 216. Switches 218, 220 are provided in each path. The receive signal processor 210 can be used in a mode in which the transducer array first transmits an ultrasound signal centered at the fundamental pass band at time $T_0$, and then later transmits ultrasound information at time $T_1$ at the harmonic pass band $2f_0$. Thus the output signal of the receive beamformer 212 at time $T_0$ includes both fundamental and harmonic components, while the output signal associated with the firing at time $T_1$ includes harmonic components without fundamental components. Depending upon the adjustment of the filters 214, 216 and the control of the switches 218, 220 many alternatives are possible. For example, information acquired in response to either of the first or the second firings at times $T_0$ and $T_1$, respectively, can be filtered to isolate the harmonic component which is applied to the image processor. The filter 214 and the switch 218 can be controlled to pass the harmonic component from the signal associated with the firing at time $T_1$ to the aberration correction value estimator, or the fundamental component from the signal associated with the firing at time $T_0$ to the aberration correction value estimator.

System Optimization Processor

As discussed above, the receive signal processor can be configured in many ways depending upon the application. For this reason, it will often be preferable to provide a system for optimizing operation of the receive signal processor to select the most appropriate mode of operation for the imaging application of interest.

One approach is to allow the user to select one of a number of pre-programmed configurations for the receive signal processor. Each configuration defines the number of beams to be formed by the receive beamformer, the filters to be used (or the filter parameters for adjustable filters), and the routing of signals to the imaging and correction paths, i.e. which switches should be closed. For example, the architecture of FIG. 14 can be programmed to operate in any of four different modes, as indicated by the four rows of Table 1. With this embodiment the user selects one of the four settings of Table 1 as a matter of preference when imaging the patient.

| Selection | Filter 54 | Filter 58 | Filter 60 | Filter 64 | Number of receive beams | Beam number selected for correction path |
|---|---|---|---|---|---|---|
| 1 | $2f_0$ WB | $2f_0$ MB | $f_0$ WB | $f_0$ NB | 2 | 2 |
| 2 | $f_0$ WB | $f_0$ MB | $2f_0$ WB | $2f_0$ NB | 2 | 2 |
| 3 | $2f_0$ WB | $2f_0$ MB | n/a | $2f_0$ NB | 1 | 1 |
| 4 | $f_0$ WB | $f_0$ MB | n/a | $f_0$ NB | 1 | 1 |

WB = wider band (e.g., 2 times BW of MB)
MB = medium band (e.g., 2 times BW of NB)
NB = narrower band (e.g., ¼ to ½ of $f_0$)

A second approach to system optimization is to use pre-set parameters for the receive signal processor that are selected automatically in response to the mode of operation of the imaging system. For example, lookup tables can be provided storing the parameters to be used for the receive signal processor under various scanning conditions. Different tables or entries in a single table can be accessed and used to program the receive signal processor depending upon the following parameters: (a) the mode of imaging (e.g. B-mode, M-mode, color Doppler mode, Doppler tissue imaging mode, etc.); (b) the transducer being used (e.g. a transesophageal transducer may best be used with the harmonic component applied to both the imaging and correction paths); (c) the depths within the image from which the echoes are being returned for both the image and the region at which aberration correction values are being calculated. In this embodiment, system parameters for the receive signal processor are automatically selected based on empirical studies pre-programmed for the given scanning conditions.

For example, aliasing and signal to noise ratios can be determined by routine experimentation, and the results of these experiments can be used to select the receive signal processor programming parameters stored in the lookup tables. Table 2 provides a rough estimate of signal levels associated with various types of signals supplied by the receive signal processor discussed above.

TABLE 2

| Imaging/Correction Mode | Relative SNR Level |
|---|---|
| B-mode imaging at fundamental | 0 dB |
| subarray correction data at fundamental | −15 dB |
| B-mode imaging at harmonic | −25 dB |
| F-mode imaging at fundamental | −40 dB |
| subarray correction data at harmonic | −40 dB |
| F-mode imaging at harmonic | −65 dB |

A third approach to optimizing a programmable receive signal processor is an automatic, adaptive system as shown in FIG. 13. In FIG. 13 the receive signal processor 230 includes a single beam receive beamformer 232, two parallel filters 234, 236 in the correction signal path and two parallel filters 238, 240 in the imaging signal path. Also included is a system optimization processor 242 that controls selection of one of the two filters 234, 236 and one of the two filters 238, 240. In this embodiment the output of the receive beamformer 232 is a broadband signal that includes both harmonic and fundamental components of the receive signal. By way of example, the filters 234, 238 may selectively pass the fundamental frequency component and the filters 236, 240 may selectively pass the harmonic frequency component. The system optimization processor 242 also receives two estimates of quality. The first estimate of quality is provided on line 244 from the aberration correction value estimator. This signal is a real time measure of the quality of the aberration correction values. The second input signal to the system optimization processor 242 is an image quality signal applied via line 246 from the image processor. The signal on line 246 is a real time measure of the quality of the image. By way of example, the quality estimates may simply be measures of the signal levels in the image and signal levels applied to the aberration correction value estimator. The system optimization processor uses the quality estimates on lines 244 and 246 to vary filter selection. The estimates of quality may be evaluated at one depth such as the gating depth for the aberration correction system or preferably at various depths throughout the image.

Figure 14:
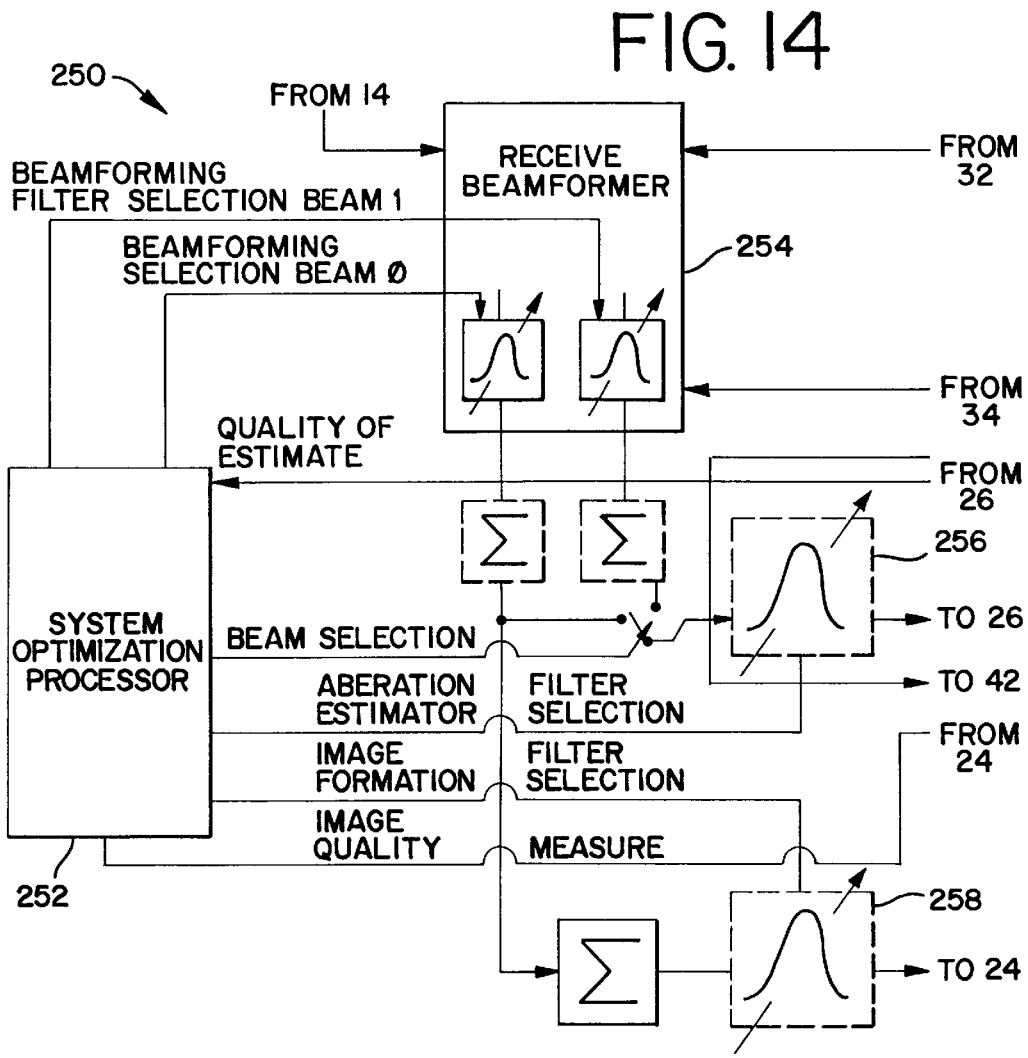

FIG. 14 shows a block diagram of another receive signal processor 250 in which the system optimization processor 252 controls beam selection from a dual beam receive beamformer 254, filter selection for the individual beams within the beamformer 254, and control settings for the filters 256, 258 in the correction and imaging paths, respectively. In the embodiment of FIG. 14, the system optimization processor 252 optimizes the filter settings, the number of beams, and the selection of beams based on real time quality measurements. In many cases, the system optimization processor 252, 242 will supply information indicative of the frequency component of the information applied to the image processor to facilitate effective image processing such as scan conversion.

Alternate Filtering Techniques

In an alternate embodiment, the following beamforming technique (known hereafter as alternate channel phasing) may be used as an alternative or a supplemental method for suppressing or filtering the fundamental signal energy. In the receive beamformer 82 of FIG. 4, the focusing delays used to calculate the second harmonic receive signals passed to the aberration value estimator are modified, so that every other channel has an additional delay equal to one cycle of the harmonic center frequency. In addition, the partial summers 92 are configured to sum signals received by an even number of channels. This delay represents a 2*pi radian phase shift at the harmonic frequency, so it has little or no impact on the harmonic signal. However, it represents a pi radian phase shift at the fundamental frequency. Since half of the summed channels experience no phase shift at the fundamental, while the other half of the summed channels experience a pi radian phase shift, the fundamental signal at the sum is effectively canceled. This may be of advantage, since it can be expensive to design and produce filters 86 for each received channel or filters 94 for each subarray signal which adequately remove the fundamental component of the received signal. This beam formation technique may either reduce the need to perform individual filtering, or increase the overall rejection of the fundamental (i.e., the degree to which the received fundamental energy is removed from the signal).

Numerous variations on this alternate channel scheme are possible. For example, the partial summers 92 of FIG. 4 may sum an odd number of channels, such as three. In this case, the fundamental would be only imperfectly canceled (for example, summing two channels with a pi phase shift and one channel with no phase shift only imperfectly cancels the fundamental). The degree of fundamental rejection may be improved by weighting the individual channel signals before summing. In the three-channel sum case, the center channel signal may be weighted twice as much as the outer channel signals.

Many other permutations are possible. Delays other than $T_2$, where $T_2$ is the period of the harmonic frequency, may be used, optionally in conjunction with weighting of the individual channel signals before summing. For example, in the three channel sum case, if a delay of 5/6*T2 is used on the two outer channels, and those same outer channels are weighted by a factor of 0.5774 before summing (where the center channel is weighted with a factor of 1), then the fundamental signal components of the summed signal will cancel, while the harmonic components are only slightly degraded. A technique such as this may be of use if the time delays that can be applied to the various channels are constrained.

This technique can be used to good effect in many of the other embodiments described herein. For example, in the architecture of FIG. 6, wherein both imaging and aberration estimation are performed at the harmonic frequency, alternate channel phasing may be used to improve the fundamental rejection of both the correction measurement signal and the imaging signal. In the architecture of FIG. 2, the technique can be used to improve fundamental rejection of the imaging signal (at the harmonic frequency) only, while the correction signal uses unperturbed focusing delays.

Less preferably, in the architectures of FIGS. 2 and 3, the technique can be used for both the imaging (harmonic frequency) and correction (fundamental frequency) paths. This may function adequately if: (1) aberration is estimated from individual element signals, or on subarrays summed from an odd number of elements, so that the cancellation is imperfect (in which case, the estimated aberration values should be corrected for the effects of the additional delays); or (2) the received fundamental signals are so much larger than the received harmonic signals that even after cancellation of the fundamental by the alternate channel phasing technique, there remains sufficient energy at the fundamental frequency. (Typically, the fundamental signal is expected to be 25–30 dB higher than the harmonic, so this case may well occur.)

Additive Inverse Embodiments

In alternate embodiments of the signal processor, the additive inverse technique is used in place of or in addition to filtering to improve the separation between linear components of a signal (components derived from linear propagation and scattering) and non-linear components (components derived from non-linear propagation or scattering such as second harmonic signals). The additive inverse technique is discussed in Chapman U.S. Pat. No. 5,632,277 and Hwang U.S. Pat. No. 5,706,819. The technique is discussed in further detail and further variations of the technique are described in U.S. Pat. No. 5,902,243 (Attorney Docket 5050/254), filed concurrently with this application and hereby incorporated by reference. As explained below, the additive inverse technique can be used to generate harmonic subarray signals from which aberration corrections are derived, or from which harmonic images are generated.

In the simplest embodiment of the additive inverse technique, two successive transmit pulses are fired along a single ultrasound line. The two pulses are identical, except that the second pulse is inverted with respect to the first pulse. For a modulated sinusoidal pulse, this is equivalent to changing the phase of the sinusoid by pi radians. For example, the two pulses may be represented as follows:

P1=e(t) * cos (2*pi*f1*t),

P2=e(t) * cos (2*pi*f1*t+pi), where e(t) represents the pulse envelope and f1 represents the transmit center frequency. From the two transmit firings, two receive waveforms Ra(t) and Rb(t) are acquired. The receive waveforms are acquired as RF, IF, or complex baseband data, and are considered here prior to any detection operation that would remove phase information and convert the receive signal to an intensity. In this specification such pre-detection signals will be referred to as "analytic" waveforms.

In general, the analytic waveforms of the receive signals associated with the two transmit events comprise fundamental and harmonic components. The two signals are in one sense quite similar. However, the fundamental and odd harmonic components of the two signals will be inverted as with the transmit pulses, while the even harmonic components will not be inverted:

Ra(t)=R1(t)+R2(t)+R3(t) . . . ,

Rb(t)=−R1(t)+R2(t)−R3(t) . . . , where R1(t), R2(t), and R3(t) are the fundamental, second harmonic, and third harmonic components, respectively, of the receive signals Ra(t), Rb(t). When the two receive signals Ra(t) and Rb(t) are added, the fundamental and odd harmonic components of the receive signals cancel, leaving primarily components arising from second harmonic propagation and scattering. When the two receive signals Ra(t), Rb(t) are subtracted, the even harmonic components cancel, and the resulting difference contains primarily components arising from linear propagation and scattering. Many variations of the additive inverse technique can be applied in conjunction with the adaptation techniques disclosed in the present specification, including those described in the above-identified related application. These variations include, but are not limited to, (1) the combination of more than two pulses to form a combined signal, the use of phase differences other than pi radians, the use of transmit pulses comprising both inverted and non-inverted components, and the use of unipolar transmit pulses, all as described in above-referenced U.S. patent application Ser. No. 09/089, 467 (Attorney Docket No. 5050/251), and (2) the use of spatially distinct transmit or receive beams, as described in U.S. patent applications Ser. Nos. 08/993,395 and 08/993, 533 (Attorney Docket Nos. 5050/255 and 5050/259).

Figure 18:
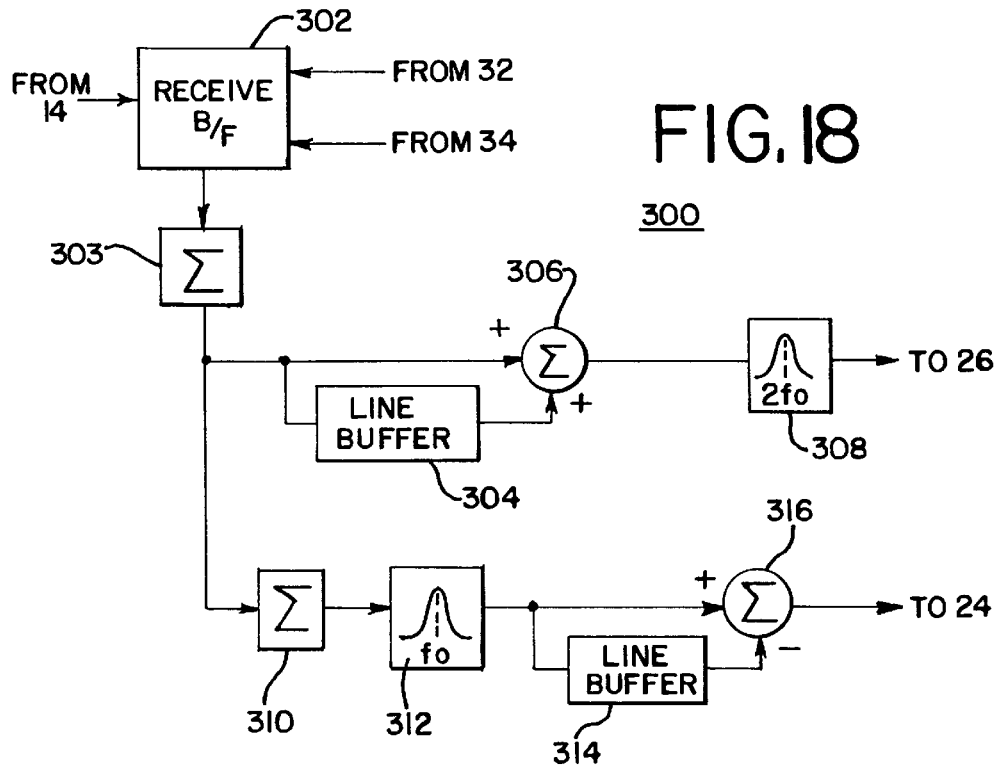
FIGS. 18 and 20 are block diagrams of alternate embodiments of receive signal processors suitable for use in the system of FIG. 1.

FIG. 18 shows one receive signal processor 300 that combines additive inverse techniques with adaptive focus correction techniques. The ultrasound imaging system that includes the signal processor 300 generates two transmit pulses of alternate polarity. The receive beamformer 302 generates as outputs analytic signals via optional subarray summer 302. The transducer element signals or the subarray signals from the first transmit firing are stored in an analytic line buffer 304. The transducer element or subarray signals from the second transmit firing are then added to the stored signals from the first transmit firing in a summer 306, using the same summing polarity for both signals to constructively reinforce the second harmonic signals or components and to cancel the fundamental components. The resulting combined or summed signal is then applied to the aberration correction path that includes the aberration correction value estimator 26, optionally via filter 308. In this embodiment the filter 308 is a passband filter arranged to pass second harmonic components while blocking fundamental components. The filtration requirements on the filter 308 are less severe than they would be if the additive inverse technique were not used. The filter 308 may be omitted or may be broader band or less deep than would otherwise be required, because a significant part of the linear components of the subarray or transducer element signals are cancelled by the additive inverse summing operation. This may be of particular advantage, as any filter 308 is repeated across all elements or all subarrays of the system. It should be noted that the analytic line buffer 304 need not store the entire receive signal for each element or subarray. Only a subset of samples (covering a limited set of ranges at which aberration correction values are to be estimated) needs to be stored and then processed by the aberration correction value estimator 26. In addition, the receive signals can be subsampled prior to storage.

On the imaging path of the signal processor 300, receive signals from the beamformer 302 are routed to beam summer 310 and are then filtered by an optional filter 312. The receive signals from the first transmit firing are stored in analytic line buffer 314. The stored signals from buffer 314 are then summed with the receive signals from the second transmit firing with opposite summing polarity in summer 316. The resulting difference signal is then stored, scan converted, and displayed by the image processor 24. Because the summer 316 operates with opposite summing polarities to emphasize the fundamental and suppress the second harmonic component, the filter 312 is a low-pass or passband filter designed to pass the fundamental components while blocking second harmonic components.

In general, the buffer 314 and summer 316 may be incorporated into the intensity processing block 36 or the motion estimator block 38 of FIG. 1. The buffer 314 and the summer 316 may also be incorporated prior to the filter 312 or prior to the beam summer 310. This may, however, increase the required size of the line buffer 314. The buffer 314 and the summer 316 may be omitted in this embodiment, as the receive signals prior to the summer 316 usually are dominated by the fundamental (linear) components of the receive signal. However, by combining the two signals the signal to noise ratio of the combined signal is increased and is therefore beneficial in some applications.

Figure 19:
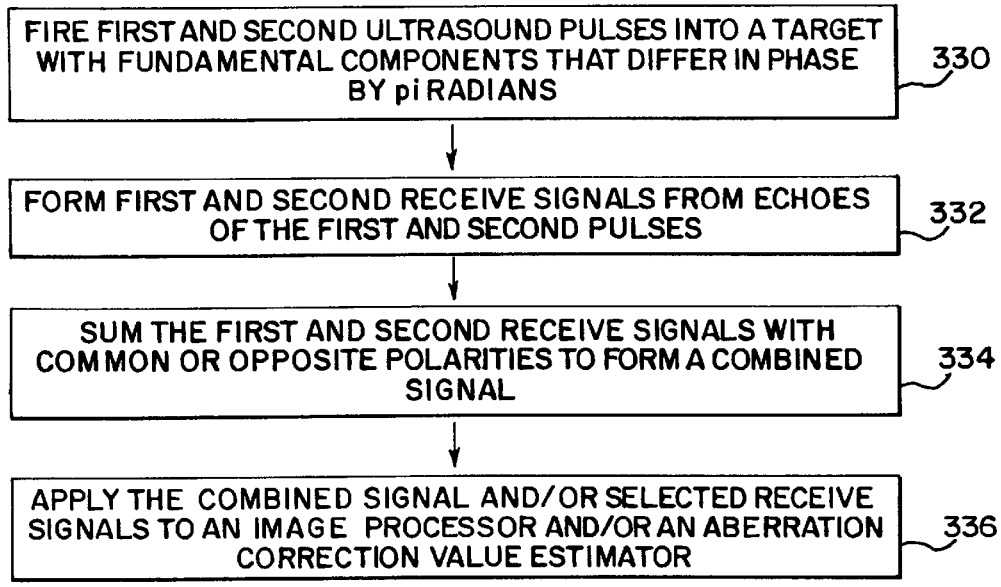
FIGS. 19 and 21 are flow charts illustrating operation of the embodiments of FIGS. 18 and 20, respectively.

FIG. 19 provides a flowchart of the operation of an ultrasonic imaging system including the receive signal processor 300 of FIG. 18. In step 330 multiple ultrasound pulses are fired into a target with fundamental components that differ in phase by about pi radians. In step 332 receive signals are formed from echoes of the ultrasound pulses of step 330, and in step 334 first and second receive signals are summed with common or opposite summing polarities to form a combined signal. In step 336 the combined signal and/or selected receive signals are applied to the image processor, to the aberration correction value estimator, or to both.

Though FIG. 18 shows one choice of signal paths and frequency bands, many others are possible. Either the fundamental or the harmonic frequency band can be applied to either the aberration correction path or the imaging signal path. Also or alternatively, a single receive signal prior to summation may be applied to either signal path. Either or both of the filters 308, 312 may be deleted if desired, and if used they may be placed either before or after the summer 306, 316. The same or different frequency bands can be applied to the imaging and aberration correction signal paths.

Figure 20:
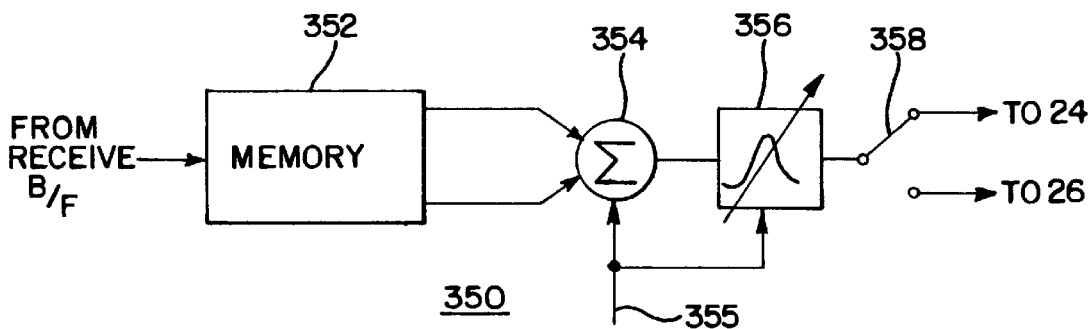

FIG. 20 shows a block diagram of another receive signal processor 350 that provides additional flexibility. The signal processor 350 is intended for use in the system of FIG. 1 described above. In the processor 350, receive signals from a receive beamformer (including receive signals from first and second transmit events that differ in phase angle by about pi radians) are stored in a memory 352. Time-aligned pairs of samples (one from the first pulse and one from the second pulse) are then retrieved from the memory 352 and applied to a summer 354. The summer 354 is controllable by a function control input 355 to sum the two inputs with either common summing polarity or opposite summing polarity as desired. The combined signal generated by the summer 354 is then optionally passed through a programmable filter 356 and via a switch 358 to either the image processor 24 or the aberration correction value estimator 26. The filter 356 is not required in all embodiments. If included as a programmable filter, it can be adjusted to selectively pass the second harmonic component or the fundamental component, depending upon the state of the control signal 355. If desired, the switch 358 can be deleted, and each signal path can be provided with a respective summer and optional filter.

Figure 21:
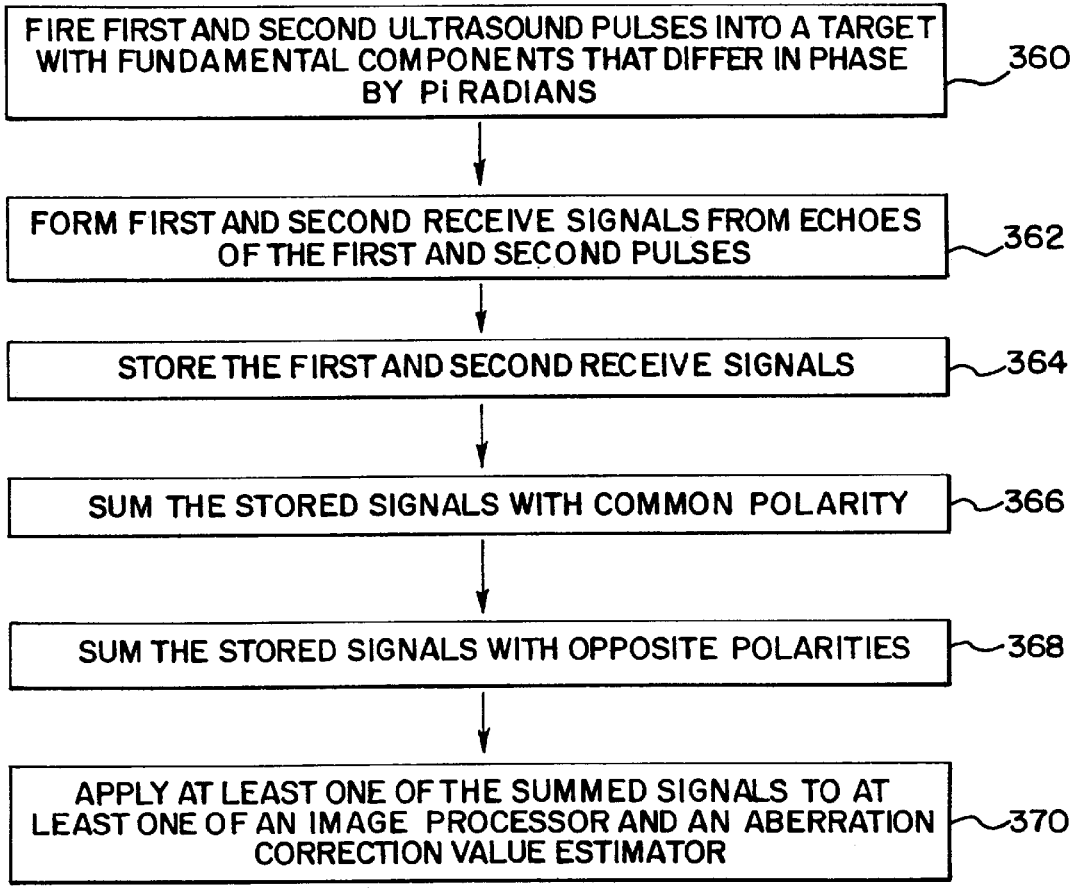

FIG. 21 provides a flow chart of the operation of an ultrasonic imaging system including the receive signal processor 350 of FIG. 20. In step 360 first and second ultrasound pulses are fired into a target with fundamental components that differ in phase by pi radians. In step 362 first and second receive signals are formed from echoes of the first and second pulses. These receive signals are stored in the memory of 352 of FIG. 20 in step 364. The stored signals from memory 352 are then summed with common polarity in summer 354 (step 366) and with opposite polarities (step 368). Then at least one of the summed or combined signals is applied to an image processor and/or an aberration correction value estimator (step 370) via the filter 356 and the switch 358 of FIG. 20.

By storing both receive signals in the memory 352, the embodiment of FIG. 20 allows both summed (non-linear) and substracted (linear) combined signals to be generated from a single set of received data. This flexibility can be used to good effect, for example by allowing a single aberration correction value estimator to estimate corrections at both a harmonic and a fundamental frequency from a single pair of firings. Alternately, a single pair of firings can be used to supply the harmonic signals, the fundamental signals, or both to the image processor 24 and the harmonic signals, the fundamental signals, or both to the aberration correction value estimator 26.

The additive inverse techniques described above can be applied to either the aberration correction value path or the imaging path or both in any of the specific embodiments disclosed in the preceding FIGS. 1–17. Where filters are included they can be made programmable or not, depending on the application, and they can be positioned before or after the various summation steps. The fundamental components can be applied to either the imaging path, the aberration correction path, or both. Similarly the harmonic components can be applied to either the imaging path, the aberration correction path, or both.

As explained above, these embodiments are not limited to the simplest versions of the additive inverse technique as described above, but can be also used with more complicated versions, as explained in co-pending U.S. Pat. No. 5,902,243 (Attorney Docket No. 5050/254).

As used herein the term "cancel" is intended broadly to encompass partial cancellation. The term "applying" is intended broadly to encompass both direct application (where a signal is applied to a downstream processor without modification) and indirect application (where a signal is modified before it is applied to a downstream processor).

Definitions

The terms discussed below are intended to be given the following meanings, both in this specification and in the following claims.

Figure 16:
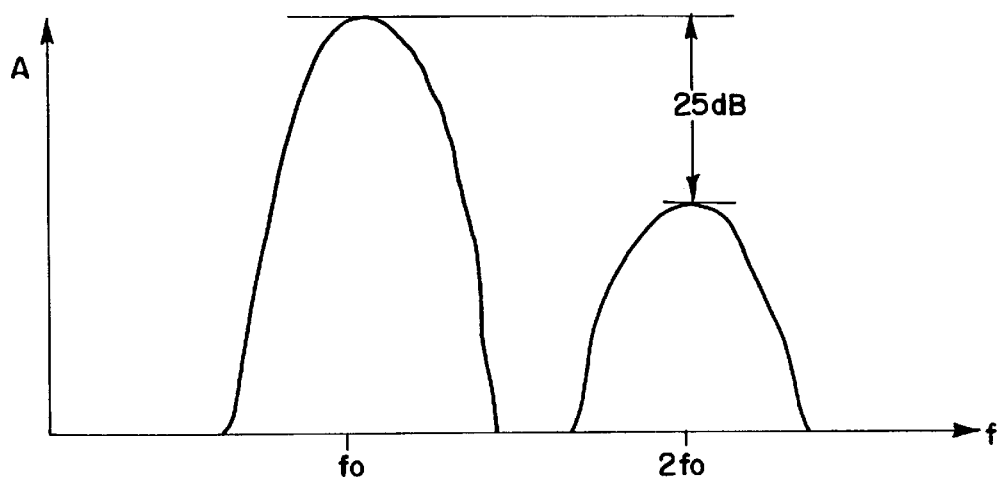
FIGS. 16 and 17 are graphs showing fundamental and harmonic components of received and filtered received waveforms, respectively.
Figure 17:
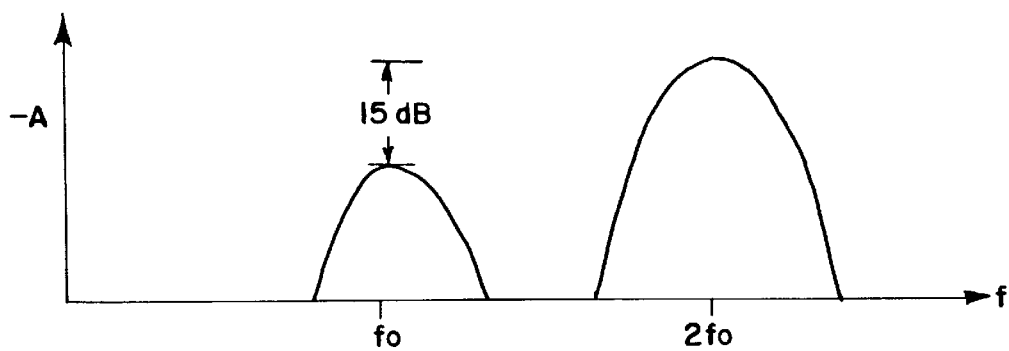

Fundamental components or information correspond to signals (whether modulated or demodulated) associated with or responsive to signals in a fundamental frequency band when ultrasonically modulated as an acoustic signal. Similarly, harmonic components or information correspond to signals (whether modulated or demodulated) associated with or responsive to signals in a harmonic frequency band when ultrasonically modulated as an acoustic signal. For example, a harmonic component may be modulated at a harmonic ultrasonic frequency such as 5 MHz, or it may be a DC signal that is responsive to the portion of a signal that was modulated at the harmonic frequency prior to demodulation. Of course, both fundamental and harmonic components will generally include measurable amounts of both. For example, FIG. 16 shows a frequency spectrum for an ultrasound signal as applied to any of the receive signal processors described above. Most of the ultrasonic energy is near the fundamental frequency $f_0$, and the harmonic peak at $2f_0$ has a peak amplitude that is reduced by 10 to 40 dB (e.g. 25 dB) from the peak amplitude at $f_0$. The harmonic component generated by the receive signal processor as described above may, for example, have a frequency spectrum as shown in FIG. 17, where the peak at $f_0$ is reduced with respect to the peak at $2f_0$ by about 3 to 40 dB (e.g. 15 dB).

Fundamental filters or pass bands selectively pass fundamental components while suppressing harmonic components, while harmonic filters or pass bands selectively pass harmonic components while suppressing fundamental components. For example, a harmonic filter may be a pass band filter centered at 5 MHz for use with a modulated signal or a low pass filter for use with a demodulated signal.

The term "pass band" is intended broadly to include low pass and high pass as well as conventional pass bands, and the frequency pass band of a signal path refers to the frequency of signals modulated at ultrasound frequencies, prior to any demodulation, regardless of whether signals leave the path in modulated or demodulated form.

"Responsive to" or "in response to" is intended broadly to encompass responsiveness, whether direct or indirect. Thus, a circuit is responsive to a signal, whether or not the signal is subjected to intermediate processing prior to being applied to the circuit.

The term "portion of an image" is intended broadly to encompass any signal that contributes to image formation, whether or not other signals are used at other times, or for other parts of the image, or in combination with the first signal.

The term "filter" is intended to encompass any means for suppressing signals outside a selected frequency band. Examples of filters include pass band filters, low pass filters, demodulators, and alternate channel phasing circuits, as described above.

The terms "selectively receiving" or "selectively transmitting" mean that substantially a majority of the energy that is processed, received, or transmitted is responsive to or corresponds to energy within a selected band of frequencies in the acoustic domain. For example, selectively receiving a harmonic component means passing the harmonic component while suppressing the fundamental component. Any of the filtering techniques described above can be used, either alone or in various combinations.

The term "harmonic" includes integer harmonics (e.g. second, third) as well as fractional harmonics and subharmonics, unless otherwise indicated.

The term "aberration correction value" is intended broadly to include focusing (phase and/or delay) and/or apodization corrections, unless otherwise indicated.

It should be understood that the foregoing detailed description has described only a few of the many forms that the present invention can take. It is therefore intended that only the following claims, including all equivalents, be regarded as a definition of the invention.

We claim:

1. An ultrasonic imaging method comprising the following steps:
   (a) transmitting ultrasonic energy into a target at a fundamental frequency band in a first transmit event,
   (b) forming at least a portion of an image in response to selectively received ultrasonic echo information associated with the first transmit event at a first frequency band; and
   (c) determining aberration correction values in response to received ultrasonic echo information associated with the first transmit event at a second frequency band, wherein one of the first and second frequency bands comprises a harmonic of the fundamental frequency band and the other of the first and second frequency bands comprises the fundamental frequency band.

2. The method of claim 1 wherein the second frequency band peaks near the fundamental frequency band, and wherein the first frequency band peaks near the harmonic of the fundamental frequency band.

3. The method of claim 1 wherein the first frequency band peaks near the fundamental frequency band, and wherein the second frequency band peaks near the harmonic of the fundamental frequency band.

4. The method of claim 1 wherein the first frequency band peaks near the harmonic of the fundamental frequency band.

5. The method of claim 1, 2, or 4 wherein the fundamental frequency band of step (a) suppresses transmission of ultrasonic energy at the harmonic.

6. The method of claim 1, 2 or 4 wherein step (b) comprises the step of filtering the echo information such that the first frequency band suppresses echo information in the fundamental frequency band.

7. The method of claim 1, or 4 wherein step (b) comprises the step of filtering the echo information to obtain the first frequency band.

8. The method of claim 7 wherein step (c) comprises the step of filtering the echo information to obtain the second frequency band.

9. The method claim 1, or 4 wherein the first frequency band comprises the harmonic of the fundamental frequency band, and wherein the portion of the image is also formed in response to echo information in the fundamental frequency band.

10. The method of claim 1 further comprising the step of maintaining the target free of additional contrast agent throughout an ultrasound imaging examination session that includes steps (a)–(c).

11. The method of claim 1 wherein the aberration correction values comprise focusing correction values.

12. The method of claim 1 wherein the aberration correction values comprise apodization correction values.

13. The method of claim 1 further comprising the step of (d) using the aberration correction values determined in step (c) in transmit to correct for aberrations associated with a second transmit event.

14. The method of claim 1 further comprising the step of (d) using the aberration correction values determined in step (c) in receive to correct for aberrations associated with a second receive event.

15. An ultrasonic imaging system comprising:
   an ultrasonic transmit beamformer coupled to a transducer array to transmit ultrasonic energy into a target at a fundamental frequency band in a first transmit event;
   an ultrasonic receive beamformer coupled to the transducer array;
   an image processor coupled to the receive beamformer, said image processor responsive to selectively received ultrasonic echo information associated with the first transmit event at a first frequency band;
   an adaptive focusing control system coupled to the receive beamformer, said adaptive focusing control system responsive to received ultrasonic echo information associated with the first transmit event at a second frequency band;
   wherein one of the first and second frequency bands peaks near a harmonic of the fundamental frequency band and the other of the first and second frequency bands peaks near the fundamental frequency band.

16. The invention of claim 15 further comprising means for suppressing transmitted ultrasonic energy near the harmonic of the fundamental frequency band; wherein the first frequency band peaks near the harmonic and suppresses the fundamental frequency band.

17. The invention of claim 16 wherein the second frequency band peaks near the fundamental frequency band.

18. The invention of claim 15 further comprising means for suppressing transmitted ultrasonic energy near the harmonic of the fundamental frequency band; wherein the second frequency band peaks near the harmonic and suppresses the fundamental frequency band.

19. The invention of claim 18 wherein the first frequency band peaks near the fundamental frequency band.

20. The invention of claim 15 wherein the adaptive focusing control system comprises means for determining focusing aberration correction values in response to said received ultrasonic echo information associated with the first transmit event at the second frequency band.

21. The invention of claim 15 wherein the adaptive focusing control system comprises means for determining apodization aberration correction values in response to said received ultrasonic echo information associated with the first transmit event at the second frequency band.

22. The invention of claim 20 or 21 further comprising means for using the aberration correction values in transmit to correct for aberrations associated with a second transmit event.

23. The invention of claim 20 or 21 further comprising means for using the aberration correction values in receive to correct for aberrations associated with a second receive event.

24. An ultrasonic imaging method comprising the following steps:
   (a) transmitting ultrasonic energy concentrated near a fundamental frequency into a target;
   (b) receiving ultrasonic energy from the target;
   (c) applying first signals derived from the ultrasonic energy received in step (b) to an image processor via a first signal path; and applying second signals derived from a portion of the ultrasonic energy received in step (b) to an aberration correction value estimator via a second signal path; said first and second signal paths characterized by differing frequency pass bands, one of said frequency pass bands peaking near a harmonic of the fundamental frequency and another of said frequency pass bands peaking near the fundamental frequency.

25. The method of claim 24 wherein the frequency pass band for the second signal path peaks near the fundamental frequency, and wherein the frequency pass band for the first signal path peaks near a harmonic of the fundamental frequency.

26. The method of claim 25 wherein the frequency pass band for the first signal path peaks near the second harmonic of the fundamental frequency.

27. The method of claim 24 wherein the frequency pass band for the first signal path peaks near the fundamental frequency, and wherein the frequency pass band for the second signal path peaks near a harmonic of the fundamental frequency.

28. The method of claim 24 wherein the frequency pass band for the first signal path peaks near a harmonic of the fundamental frequency.

29. The method of claim 25 or 28 wherein step (a) comprises the step of suppressing the transmitted ultrasonic energy at the harmonic of the fundamental frequency.

30. The method of claim 24 wherein step (c) comprises the step of including a filter in the first signal path to suppress ultrasonic energy received in step (b) at the fundamental frequency band.

31. The method of claim 24, 25, 26, 28, or 30 comprising the further step of (d) providing a first filter in the first signal path.

32. The method of claim 31 comprising the step of (e) providing a second filter in the second signal path.

33. The method of claim 24 wherein the first signal path comprises a first component path characterized by a harmonic pass band and a second component path characterized by a fundamental pass band.

34. The method of claim 28 further comprising the step of maintaining the target free of additional contrast agent throughout an ultrasound imaging examination session that includes steps (a)–(c).

35. An ultrasonic imaging system comprising:
an ultrasonic transmit beamformer coupled to a transducer array and operative to transmit ultrasonic energy concentrated near a fundamental frequency into a target;
an ultrasonic receive signal processor coupled to the transducer array, responsive to received echo information from the target, and comprising first and second signal paths characterized by differing frequency pass bands, one of said frequency pass bands peaking near a harmonic of the fundamental frequency and another of said frequency pass bands peaking near the fundamental frequency;
an image processor coupled to the first signal path of the receive signal processor;
an adaptive focusing control system coupled to the second signal path of the receive signal processor.

36. The invention of claim 35 wherein the transmit beamformer comprises means for suppressing transmitted ultrasonic energy in a harmonic band; and wherein the pass band of the first signal path peaks in the harmonic band and suppresses ultrasonic energy in the fundamental band.

37. The invention of claim 35 wherein the pass band of the second signal path peaks near the fundamental band.

38. The invention of claim 35 wherein the transmit beamformer comprises means for suppressing transmitted ultrasonic energy in a harmonic band; and wherein the pass band of the second signal path peaks in the harmonic band and suppresses ultrasonic energy in the fundamental band.

39. The invention of claim 38 wherein the pass band of the first signal path peaks near the fundamental band.

40. The invention of claim 35 wherein the first and second signal paths comprise first and second filters, respectively, said filters characterized by differing pass bands.

41. An ultrasonic imaging method comprising the following steps:
(a) selectively transmitting ultrasonic energy concentrated near a transmit frequency into a target;
(b) selectively receiving ultrasonic energy concentrated near a first receive frequency from the target;
(c) using signals received in step (b) to calculate aberration correction values;
(d) selectively receiving ultrasonic energy concentrated near a second receive frequency from the target, step (d) comprising the step of applying the aberration correction values calculated in step (c) to enhance focus of the selectively received ultrasonic energy concentrated near the second receive frequency;
said first and second receive frequencies differing from one another, one of said first and second receive frequencies being a harmonic of the transmit frequency and another of said first and second receive frequencies being the transmit frequency.

42. The method of claim 41 wherein the second receive frequency is a second harmonic of the first receive frequency.

43. The method of claim 41 further comprising the step of maintaining the target free of additional contrast agent throughout an ultrasound imaging examination session that includes steps (a)–(d).

44. The method of claim 41 wherein said ultrasonic energy is transmitted into the target in a plurality of transmit events in step (a), and wherein steps (c) and (d) are associated with different transmit events.

45. An ultrasonic imaging method comprising the following steps:
(a) transmitting a first ultrasound firing at a lower frequency band;
(b) receiving first ultrasound echo information from the first firing at a higher frequency band;
(c) forming at least a portion of an image in response to the first ultrasound echo information;
(d) transmitting a second ultrasound firing at the lower frequency band;
(e) receiving second ultrasound echo information from the second firing at the lower frequency band; and
(f) determining aberration correction values in response to the second ultrasound echo information.

46. The method of claim 45 wherein the higher frequency band is at a harmonic of the lower frequency band.

47. The method of claim 45 further comprising the step of maintaining the target free of additional contrast agent throughout an ultrasound imaging examination session that includes steps (a)–(f).

48. An ultrasonic imaging method comprising the following steps:
(a) transmitting a first ultrasound firing at a fundamental frequency band;
(b) receiving first ultrasound echo information from the first firing at a harmonic frequency band;
(c) forming at least a portion of an image in response to the first ultrasound echo information;

(d) transmitting a second ultrasound firing at the fundamental frequency band;

(e) receiving second ultrasound echo information from the second firing at the fundamental frequency band; and (f) determining aberration correction values in response to the second ultrasound echo information.

49. The method of claim 48 further comprising the step of maintaining the target free of additional contrast agent throughout an ultrasound imaging examination session that includes steps (a)–(f).

50. An ultrasonic imaging method comprising the following steps:

(a) transmitting an ultrasound signal;

(b) receiving a wide band ultrasound echo signal;

(c) filtering the echo signal to form a first low frequency component and a second high frequency component;

(d) forming at least part of an image at least in part in response to the second high frequency component;

(e) determining aberration correction values at least in part in response, to the first low frequency component, wherein the first and second components are characterized by respective first and second frequency bands, and wherein the second frequency band is a harmonic of the first frequency band.

51. The method of claim 50 further comprising the step of maintaining the target free of additional contrast agent throughout an ultrasound imaging examination session that includes steps (a)–(e).

52. An ultrasonic imaging method comprising the following steps:

(a) transmitting ultrasonic energy into a target at a fundamental frequency band in a first transmit event, (b) forming at least a portion of an image in response to selectively received ultrasonic echo information associated with the first transmit event at a first frequency band; and (c) determining aberration correction values in response to received ultrasonic echo information associated with the first transmit event at a second frequency band, wherein at least one of the first and second frequency bands comprises a harmonic of the fundamental frequency band;

(d) maintaining the target free of additional contrast agent throughout an ultrasound imaging examination session that includes steps (a)–(c).

* * * * *